(12) United States Patent
Bednarek

(10) Patent No.: US 7,819,866 B2
(45) Date of Patent: Oct. 26, 2010

(54) ABLATION CATHETER AND ELECTRODE

(75) Inventor: Michael C. Bednarek, Buffalo, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 697 days.

(21) Appl. No.: 10/645,892

(22) Filed: Aug. 20, 2003

(65) Prior Publication Data

US 2004/0143256 A1 Jul. 22, 2004

Related U.S. Application Data

(60) Provisional application No. 60/441,980, filed on Jan. 21, 2003.

(51) Int. Cl.
*A61B 18/14* (2006.01)

(52) U.S. Cl. .................................. 606/41; 607/101

(58) Field of Classification Search .............. 606/41, 606/48–50; 607/101–105
See application file for complete search history.

(56) References Cited

U.S. PATENT DOCUMENTS

| | | | | |
|---|---|---|---|---|
| 4,641,649 A | | 2/1987 | Walinsky et al. | 128/303.1 |
| 4,776,334 A | * | 10/1988 | Prionas | 606/42 |
| 4,860,769 A | * | 8/1989 | Fogarty et al. | 607/119 |
| 4,896,671 A | | 1/1990 | Cunningham et al. | 128/642 |
| 4,934,049 A | | 6/1990 | Kiekhafer et al. | 29/883 |
| 4,945,912 A | | 8/1990 | Langberg | 128/642 |
| 4,976,711 A | * | 12/1990 | Parins et al. | 606/48 |
| 5,125,895 A | | 6/1992 | Buchbinder et al. | 604/95 |
| 5,125,896 A | | 6/1992 | Hojeibane | 604/95 |
| 5,209,229 A | | 5/1993 | Gilli | 128/419 |
| 5,228,442 A | | 7/1993 | Imran | 128/642 |
| 5,231,995 A | | 8/1993 | Desai | 128/784 |
| 5,239,999 A | | 8/1993 | Imran | 128/642 |
| 5,242,441 A | | 9/1993 | Avitall | 606/41 |
| 5,246,438 A | | 9/1993 | Langberg | 606/33 |
| 5,255,679 A | | 10/1993 | Imran | 128/642 |
| 5,263,493 A | | 11/1993 | Avitall | 607/122 |
| 5,269,757 A | | 12/1993 | Fagan et al. | 604/95 |
| RE34,502 E | | 1/1994 | Webster, Jr. | 607/1 |
| 5,277,199 A | | 1/1994 | DuBois et al. | 128/772 |
| 5,279,299 A | | 1/1994 | Imran | 128/642 |

(Continued)

FOREIGN PATENT DOCUMENTS

WO    WO 95/10319    4/1995

*Primary Examiner*—Michael Peffley
(74) *Attorney, Agent, or Firm*—Heimbecher & Assoc., LLC

(57) ABSTRACT

An ablation catheter including a shaft supporting one or more partially or completely exposed braided electrodes that may be positioned against a target tissue to ablate the tissue. The shaft may be precurved in a loop-like shape or any other shape to assist in positioning the electrode against a target tissue. The shaft may include a fluid lumen to direct a fluid material, which may be conductive, through one or more apertures or ports. The ports are adapted to direct the fluid past portions of the braided electrode to cool the electrode, flush blood away from the electrode, and to transfer ablation energy to the target tissue. Ablation energy may be delivered directly by the electrode and by way of a conductive fluid contacting the electrode. The shaft may further include a second lumen to provide a housing for a control wire that may be used to control the shape of the shaft.

23 Claims, 12 Drawing Sheets

U.S. PATENT DOCUMENTS

| | | | |
|---|---|---|---|
| 5,281,213 A | 1/1994 | Milder et al. | 606/15 |
| 5,281,217 A | 1/1994 | Edwards et al. | 606/41 |
| 5,293,868 A | 3/1994 | Nardella | 128/642 |
| 5,311,866 A | 5/1994 | Kagan et al. | 128/642 |
| 5,318,525 A | 6/1994 | West et al. | 604/95 |
| 5,324,284 A | 6/1994 | Imran | 606/15 |
| 5,327,889 A | 7/1994 | Imran | 128/642 |
| 5,327,905 A | 7/1994 | Avitall | 128/772 |
| 5,330,466 A | 7/1994 | Imran | 606/13 |
| 5,334,193 A | 8/1994 | Nardella | 606/41 |
| 5,345,936 A | 9/1994 | Pomeranz et al. | 128/642 |
| 5,348,554 A | 9/1994 | Imran et al. | 606/41 |
| 5,354,297 A | 10/1994 | Avitall | 606/45 |
| 5,383,923 A | 1/1995 | Webster, Jr. | 607/125 |
| 5,389,073 A | 2/1995 | Imran | 604/95 |
| 5,391,147 A | 2/1995 | Imran et al. | 604/95 |
| 5,395,328 A | 3/1995 | Ockuly et al. | 604/95 |
| 5,396,887 A | 3/1995 | Imran | 128/642 |
| 5,397,304 A * | 3/1995 | Truckai | 604/528 |
| 5,405,376 A | 4/1995 | Mulier et al. | 607/127 |
| 5,406,946 A | 4/1995 | Imran | 128/642 |
| 5,409,000 A | 4/1995 | Imran | 128/642 |
| 5,411,025 A * | 5/1995 | Webster, Jr. | 600/374 |
| 5,415,166 A | 5/1995 | Imran | 128/642 |
| 5,423,772 A | 6/1995 | Lurie et al. | 604/282 |
| 5,423,811 A | 6/1995 | Imran et al. | 606/41 |
| 5,423,882 A | 6/1995 | Jackman et al. | 607/122 |
| 5,431,168 A | 7/1995 | Webster, Jr. | 128/658 |
| 5,431,649 A | 7/1995 | Mulier et al. | 606/41 |
| 5,433,708 A * | 7/1995 | Nichols et al. | 604/113 |
| 5,445,148 A | 8/1995 | Jaraczewski et al. | 128/642 |
| 5,465,717 A | 11/1995 | Imran et al. | 128/642 |
| 5,478,330 A | 12/1995 | Imran et al. | 604/282 |
| 5,487,385 A | 1/1996 | Avitall | 128/642 |
| 5,487,757 A | 1/1996 | Truckai et al. | 607/122 |
| 5,522,873 A | 6/1996 | Jackman et al. | 607/122 |
| 5,527,279 A | 6/1996 | Imran | 604/95 |
| 5,533,967 A | 7/1996 | Imran | 604/95 |
| 5,540,681 A | 7/1996 | Strul et al. | 606/34 |
| 5,542,928 A | 8/1996 | Evans et al. | 604/113 |
| 5,545,161 A | 8/1996 | Imran | 606/41 |
| 5,545,200 A | 8/1996 | West et al. | 607/122 |
| 5,549,581 A | 8/1996 | Lurie et al. | 604/282 |
| 5,558,073 A | 9/1996 | Pomeranz et al. | 128/642 |
| 5,562,619 A | 10/1996 | Mirarchi et al. | 604/95 |
| 5,571,088 A | 11/1996 | Lennox et al. | 604/96 |
| 5,573,533 A | 11/1996 | Strul | 606/34 |
| 5,575,772 A | 11/1996 | Lennox | 604/96 |
| 5,578,007 A | 11/1996 | Imran | 604/95 |
| 5,582,609 A * | 12/1996 | Swanson et al. | 606/39 |
| 5,584,830 A | 12/1996 | Ladd et al. | 606/34 |
| 5,584,872 A | 12/1996 | LaFontaine et al. | 607/116 |
| 5,588,964 A | 12/1996 | Imran et al. | 604/95 |
| 5,609,151 A | 3/1997 | Mulier et al. | 128/642 |
| 5,611,777 A | 3/1997 | Bowden et al. | 604/95 |
| 5,628,313 A | 5/1997 | Webster, Jr. | 128/642 |
| 5,643,197 A * | 7/1997 | Brucker et al. | 604/20 |
| 5,643,231 A | 7/1997 | Lurie et al. | 604/282 |
| 5,656,029 A | 8/1997 | Imran et al. | 604/95 |
| 5,656,030 A | 8/1997 | Hunjan et al. | 604/95 |
| 5,658,278 A | 8/1997 | Imran et al. | 606/41 |
| 5,676,662 A | 10/1997 | Fleischhacker et al. | 606/41 |
| 5,676,693 A | 10/1997 | LaFontaine | 607/116 |
| 5,680,860 A | 10/1997 | Imran | 128/642 |
| 5,697,927 A | 12/1997 | Imran et al. | 606/41 |
| 5,715,817 A | 2/1998 | Stevens-Wright et al. | 128/642 |
| 5,722,401 A | 3/1998 | Pietroski et al. | 128/642 |
| 5,722,963 A | 3/1998 | Lurie et al. | 604/282 |
| 5,730,128 A | 3/1998 | Pomeranz et al. | 128/642 |
| 5,755,760 A | 5/1998 | Maquire et al. | 607/122 |
| 5,779,669 A | 7/1998 | Haissaguerre et al. | 604/95 |
| 5,779,699 A | 7/1998 | Lipson | 606/41 |
| 5,782,239 A | 7/1998 | Webster, Jr. | 128/642 |
| 5,782,828 A | 7/1998 | Chen et al. | 606/42 |
| 5,782,899 A | 7/1998 | Imran | 607/122 |
| 5,785,706 A | 7/1998 | Bednarek | 606/41 |
| RE35,880 E | 8/1998 | Waldman et al. | 600/374 |
| 5,792,140 A | 8/1998 | Tu et al. | 606/41 |
| 5,800,482 A | 9/1998 | Pomeranz et al. | 607/101 |
| 5,807,249 A | 9/1998 | Qin et al. | 600/374 |
| 5,807,395 A | 9/1998 | Mulier et al. | 606/41 |
| 5,814,029 A | 9/1998 | Hassett | 604/281 |
| 5,820,568 A | 10/1998 | Willis | 600/523 |
| 5,823,955 A | 10/1998 | Kuck et al. | 600/374 |
| 5,826,576 A * | 10/1998 | West | 600/373 |
| 5,827,272 A | 10/1998 | Breining et al. | 606/41 |
| 5,836,875 A | 11/1998 | Webster, Jr. | 600/374 |
| 5,836,947 A | 11/1998 | Fleischman et al. | 606/47 |
| 5,842,984 A | 12/1998 | Avitall | 600/374 |
| 5,843,020 A | 12/1998 | Tu et al. | 604/22 |
| 5,860,974 A | 1/1999 | Abele | 606/41 |
| 5,865,800 A | 2/1999 | Mirarchi et al. | 604/95 |
| 5,868,733 A | 2/1999 | Ockuly et al. | 606/10 |
| 5,868,741 A | 2/1999 | Chia et al. | 606/41 |
| 5,876,340 A | 3/1999 | Tu et al. | 600/439 |
| 5,876,398 A | 3/1999 | Mulier et al. | 606/41 |
| 5,876,399 A | 3/1999 | Chia et al. | 606/41 |
| 5,879,296 A | 3/1999 | Ockuly et al. | 600/374 |
| 5,882,346 A | 3/1999 | Pomeranz et al. | 604/280 |
| 5,885,278 A | 3/1999 | Fleischman et al. | 606/41 |
| 5,891,027 A | 4/1999 | Tu et al. | 606/41 |
| 5,891,137 A | 4/1999 | Chia et al. | 606/41 |
| 5,893,885 A | 4/1999 | Webster, Jr. | 607/122 |
| 5,895,355 A * | 4/1999 | Schaer | 600/381 |
| 5,895,417 A | 4/1999 | Pomeranz et al. | 607/101 |
| 5,897,529 A | 4/1999 | Ponzi | 604/95 |
| 5,897,554 A | 4/1999 | Chia et al. | 606/41 |
| 5,906,605 A | 5/1999 | Coxum | 604/525 |
| 5,908,446 A | 6/1999 | Imran | 607/122 |
| 5,910,129 A | 6/1999 | Koblish et al. | 604/95 |
| 5,913,854 A | 6/1999 | Maguire et al. | 606/41 |
| 5,913,856 A | 6/1999 | Chia et al. | 606/41 |
| 5,916,158 A | 6/1999 | Webster, Jr. | 600/374 |
| 5,916,213 A | 6/1999 | Haissaguerre et al. | 606/41 |
| 5,916,214 A | 6/1999 | Cosio et al. | 606/41 |
| 5,919,188 A | 7/1999 | Shearon et al. | 606/41 |
| 5,921,924 A | 7/1999 | Avitall | 600/374 |
| 5,931,811 A | 8/1999 | Haissaguerre et al. | 604/95 |
| 5,935,102 A | 8/1999 | Bowden et al. | 604/95 |
| 5,935,124 A | 8/1999 | Klumb et al. | 606/42 |
| 5,938,603 A | 8/1999 | Ponzi | 600/424 |
| 5,938,659 A | 8/1999 | Tu et al. | 606/41 |
| 5,938,660 A | 8/1999 | Swartz et al. | 606/45 |
| 5,938,694 A | 8/1999 | Jaraczewski et al. | 607/122 |
| 5,944,690 A | 8/1999 | Falwell et al. | 604/95 |
| 5,951,471 A * | 9/1999 | de la Rama et al. | 600/381 |
| 5,964,796 A | 10/1999 | Imran | 607/122 |
| 5,971,968 A | 10/1999 | Tu et al. | 604/264 |
| 5,971,983 A | 10/1999 | Lesh | 606/41 |
| 5,987,344 A | 11/1999 | West | 600/373 |
| 5,993,462 A | 11/1999 | Pomeranz et al. | 606/129 |
| 6,001,085 A | 12/1999 | Lurie et al. | 604/282 |
| 6,002,955 A | 12/1999 | Willems et al. | 600/374 |
| 6,004,269 A | 12/1999 | Crowley et al. | 600/439 |
| 6,010,500 A | 1/2000 | Sherman et al. | 606/41 |
| 6,012,457 A | 1/2000 | Lesh | 128/898 |
| 6,014,579 A | 1/2000 | Pomeranz et al. | 600/374 |
| 6,015,407 A | 1/2000 | Rieb et al. | 606/41 |
| 6,016,437 A | 1/2000 | Tu et al. | 600/374 |
| 6,023,638 A | 2/2000 | Swanson | 600/510 |
| 6,024,740 A | 2/2000 | Lesh et al. | 606/34 |
| 6,027,473 A | 2/2000 | Ponzi | 604/95 |
| 6,029,091 A | 2/2000 | de la Rama et al. | 607/102 |
| 6,032,061 A | 2/2000 | Koblish | 600/372 |

| Patent No. | Date | Inventor | Class |
|---|---|---|---|
| 6,032,077 A | 2/2000 | Pomeranz | 607/101 |
| 6,033,403 A | 3/2000 | Tu et al. | 606/41 |
| 6,048,329 A | 4/2000 | Thompson et al. | 604/95 |
| 6,059,739 A | 5/2000 | Baumann | 600/585 |
| 6,063,022 A | 5/2000 | Ben-Haim | 600/41 |
| 6,063,080 A | 5/2000 | Nelson et al. | 606/41 |
| 6,064,902 A | 5/2000 | Haissaguerre et al. | 600/381 |
| 6,064,905 A | 5/2000 | Webster, Jr. et al. | 600/424 |
| 6,066,125 A | 5/2000 | Webster, Jr. | 604/528 |
| 6,068,629 A | 5/2000 | Haissaguerre et al. | 606/41 |
| 6,068,653 A | 5/2000 | LaFontaine | 607/116 |
| 6,071,274 A | 6/2000 | Thompson et al. | 604/528 |
| 6,071,279 A | 6/2000 | Whayne et al. | 606/41 |
| 6,071,282 A | 6/2000 | Fleischman | 606/41 |
| 6,076,012 A | 6/2000 | Swanson et al. | 604/21 |
| 6,078,830 A * | 6/2000 | Levin et al. | 600/374 |
| 6,080,151 A * | 6/2000 | Swartz et al. | 606/45 |
| 6,083,222 A | 7/2000 | Klein et al. | 606/41 |
| 6,090,104 A | 7/2000 | Webster, Jr. | 606/41 |
| 6,117,101 A | 9/2000 | Diederich et al. | 604/22 |
| 6,119,041 A | 9/2000 | Pomeranz et al. | 607/101 |
| 6,120,476 A | 9/2000 | Fung et al. | 604/95 |
| 6,120,500 A * | 9/2000 | Bednarek et al. | 606/41 |
| 6,123,699 A | 9/2000 | Webster, Jr. | 604/528 |
| 6,132,426 A | 10/2000 | Kroll | 606/41 |
| 6,138,043 A | 10/2000 | Avitall | 600/377 |
| 6,146,338 A | 11/2000 | Gardeski et al. | 600/585 |
| 6,156,034 A | 12/2000 | Cosio et al. | 606/41 |
| 6,164,283 A | 12/2000 | Lesh | 128/898 |
| 6,168,594 B1 | 1/2001 | LaFontaine et al. | 606/41 |
| 6,169,916 B1 | 1/2001 | West | 600/373 |
| 6,171,275 B1 | 1/2001 | Webster, Jr. | 604/20 |
| 6,171,277 B1 | 1/2001 | Ponzi | 604/95.04 |
| 6,183,435 B1 | 2/2001 | Bumbalough et al. | 604/95.01 |
| 6,183,463 B1 | 2/2001 | Webster, Jr. | 604/528 |
| 6,198,974 B1 | 3/2001 | Webster, Jr. | 607/122 |
| 6,200,315 B1 | 3/2001 | Gaiser et al. | 606/41 |
| 6,203,507 B1 | 3/2001 | Wadsworth et al. | 600/585 |
| 6,203,525 B1 | 3/2001 | Whayne et al. | 604/95.01 |
| 6,210,362 B1 | 4/2001 | Ponzi | 604/95.01 |
| 6,210,406 B1 | 4/2001 | Webster | 606/41 |
| 6,210,407 B1 | 4/2001 | Webster | 606/41 |
| 6,214,002 B1 | 4/2001 | Fleischman et al. | 606/41 |
| 6,217,528 B1 | 4/2001 | Koblish et al. | 600/585 |
| 6,217,573 B1 | 4/2001 | Webster | 606/41 |
| 6,217,574 B1 | 4/2001 | Webster | 606/41 |
| 6,217,576 B1 | 4/2001 | Tu et al. | 606/41 |
| 6,219,582 B1 | 4/2001 | Hofstad et al. | 607/122 |
| 6,221,070 B1 | 4/2001 | Tu et al. | 606/41 |
| 6,224,587 B1 | 5/2001 | Gibson | 604/528 |
| 6,233,477 B1 | 5/2001 | Chia et al. | 600/424 |
| 6,235,025 B1 | 5/2001 | Swartz et al. | 606/45 |
| 6,238,393 B1 | 5/2001 | Mulier et al. | 606/41 |
| 6,241,722 B1 | 6/2001 | Dobak et al. | 606/23 |
| 6,241,726 B1 | 6/2001 | Chia et al. | 606/41 |
| 6,241,727 B1 | 6/2001 | Tu et al. | 606/41 |
| 6,241,754 B1 | 6/2001 | Swanson et al. | 607/99 |
| 6,245,064 B1 | 6/2001 | Lesh et al. | 606/34 |
| 6,251,109 B1 | 6/2001 | Hasset et al. | 606/45 |
| 6,254,599 B1 | 7/2001 | Lesh et al. | 606/41 |
| 6,264,654 B1 | 7/2001 | Swartz et al. | 606/45 |
| 6,287,306 B1 | 9/2001 | Kroll et al. | 606/41 |
| 6,290,697 B1 | 9/2001 | Tu et al. | 606/27 |
| 6,305,378 B1 | 10/2001 | Lesh | 128/898 |
| 6,308,091 B1 | 10/2001 | Avitall | 600/374 |
| 6,314,962 B1 | 11/2001 | Vaska et al. | 128/898 |
| 6,314,963 B1 | 11/2001 | Vaska et al. | 128/898 |
| 6,325,797 B1 * | 12/2001 | Stewart et al. | 606/41 |
| 6,330,473 B1 | 12/2001 | Swanson et al. | 604/21 |
| 6,371,955 B1 | 4/2002 | Fuimaono et al. | 606/41 |
| 6,375,654 B1 | 4/2002 | McIntyre | 606/41 |
| 6,383,151 B1 | 5/2002 | Diederich et al. | 601/2 |
| 6,391,024 B1 * | 5/2002 | Sun et al. | 606/34 |
| 6,402,746 B1 | 6/2002 | Whayne et al. | 606/41 |
| 6,409,722 B1 | 6/2002 | Hoey et al. | 606/34 |
| 6,416,511 B1 | 7/2002 | Lesh et al. | 606/41 |
| 6,447,507 B1 | 9/2002 | Bednarek et al. | 606/41 |
| 6,454,758 B1 | 9/2002 | Thompson et al. | 604/528 |
| 6,454,766 B1 | 9/2002 | Swanson et al. | 606/41 |
| 6,466,811 B1 | 10/2002 | Hassett | 600/374 |
| 6,503,247 B2 | 1/2003 | Swartz et al. | 606/41 |
| 6,540,744 B2 | 4/2003 | Hassett et al. | 606/45 |
| 6,626,136 B2 | 9/2003 | Mikame et al. | 128/642 |
| 6,692,492 B2 * | 2/2004 | Simpson et al. | 606/41 |
| 6,837,886 B2 * | 1/2005 | Collins et al. | 606/41 |
| 2002/0026187 A1 * | 2/2002 | Swanson | 606/41 |

* cited by examiner

ABLATION CATHETER AND ELECTRODE

CROSS-REFERENCE TO RELATED APPLICATIONS

This application is a non-provisional application claiming priority to provisional application No. 60/441,980 titled "Ablation Catheter and Electrode," filed Jan. 21, 2003, the disclosure of which is hereby incorporated by reference in its entirety.

BACKGROUND OF INVENTION a. Field of the Invention

The present invention relates generally to the field of catheter ablation, and more particularly to an ablation catheter arrangement.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel located near the surface of a human body and is guided to a specific location within the body for examination, diagnosis, and treatment. For example, one procedure often referred to as "catheter ablation" utilizes a catheter to convey an electrical stimulus to a selected location within the human body to create necrosis, which is commonly referred to as ablation of cardiac tissue. Another procedure oftentimes referred to as "mapping" utilizes a catheter with sensing electrodes to monitor various forms of electrical activity in the human body.

Catheters are used increasingly for medical procedures involving the human heart. As illustrated in FIG. 1, a typical human heart 10 includes a right ventricle 12, a right atrium 14, a left ventricle 16 and a left atrium 18. The right atrium is in fluid communication with the superior vena cava 20 and the inferior vena cava 22. The interatrial septum 24 separates the right atrium from the left atrium. The tricuspid valve 26 contained within the atrioventricular septum provides a fluid flow path between the right atrium with the right ventricle. On the inner wall of the right atrium where it is connected with the left atrium is a thin walled, recessed area, referred to as the fossa ovalis 28. Between the fossa ovalis and the tricuspid valve is the opening or ostium for the coronary sinus 30. The coronary sinus is the large epicardial vein which accommodates most of the venous blood which drains from the myocardium into the right atrium.

In a normal heart, contraction and relaxation of the heart muscle (myocardium) takes place in an organized fashion as electrochemical signals pass sequentially through the myocardium from the sinoatrial (SA) node (not shown) located in the right atrium to the atrialventricular (AV) node (not shown) and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve 26 through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the atrium which are referred to as atrial arrhythmia. Three of the most common arrhythmia are ectopic atrial tachycardia, atrial fibrillation and atrial flutter. Atrial fibrillation can result in significant patient discomfort and even death because of a number of associated problems, including the following: (1) an irregular heart rate, which causes a patient discomfort and anxiety, (2) loss of synchronous atrioventricular contractions which compromises cardiac hemodynamics resulting in varying levels of congestive heart failure, and (3) stasis of blood flow, which increases the vulnerability to thromboembolism. It is sometimes difficult to isolate a specific pathological cause for the atrial fibrillation although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included significant usage of various drugs. In some circumstances drug therapy is ineffective and frequently is plagued with side effects such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. Such procedures are performed many times with an ablation catheter. Typically, the ablation catheter is inserted in an artery or vein in the leg, neck, or arm of the patient and threaded, sometimes with the aid of a guidewire or introducer, through the vessels until a distal tip of the ablation catheter reaches the desired location for the ablation procedure in the heart. The ablation catheters commonly used to perform these ablation procedures produce lesions and electrically isolate or render the tissue non-contractile at particular points in the cardiac tissue by physical contact of the cardiac tissue with an electrode of the ablation catheter and application of energy. The lesion partially or completely blocks the stray electrical signals to lessen or eliminate atrial fibrillations.

In some conventional ablation procedures, the ablation catheter includes a plurality of electrodes with a single distal electrode secured to the tip of the ablation catheter to produce small lesions wherever the tip contacts the tissue. To produce a linear lesion, the tip may be dragged slowly along the tissue during energy application. Increasingly, however, cardiac ablation procedures utilize multiple electrodes affixed to the catheter body to form multiple lesions.

One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface. Without such continuous and uniform contact, any ablation lesions formed may not be adequate.

Moreover, effective ablation procedures are sometimes quite difficult because of the need for an extended linear lesion, sometimes as long as about three inches to five inches (approximately eight centimeters to twelve centimeters). To produce such a linear lesion of this length within an erratically beating heart is a difficult task. In some instances, stray electrical signals find a pathway down the pulmonary veins 32 and into the left atrium. In these instances, it may be desirable to produce a circumferential lesion at the ostium 34 to one or more of the pulmonary veins or within one or more of the pulmonary veins. The pulmonary veins may reach a circumference of up to about ten centimeters; thus, a ten centimeter circumferential lesion would be desirable to completely block stray signals from traveling down the pulmonary vein and into the left atrium.

SUMMARY OF INVENTION

The present invention involves an ablation catheter, and in one form, comprises a catheter shaft and at least one braided electrode. The catheter shaft defines an inner surface and an outer surface. The braided electrode is interposed between the inner surface and the outer surface. The outer surface defines at least one braided electrode aperture such that a portion of the braided electrode is exposed. The catheter shaft may further define a lumen. The inner surface of the catheter shaft may further define at least one fluid aperture providing a fluid flow path past the braided cathode.

The ablation catheter may be connected with a fluid introduction system in fluid communication with the lumen. The introduction system is configured to provide a fluid material to the lumen. The lumen is configured to guide the fluid media through the at least one fluid aperture or port. The fluid aperture is located so as to guide the fluid media past the braided electrode substantially to move blood away from the braided electrode to lessen formation of coagulum. The fluid media may be a conductive media. As such, the conductive fluid media is configured to flow past the at least one braided electrode and conduct ablative energy to a target tissue and ablate, in part, through ohmic energy.

The braided electrode aperture or window, in one implementation, has a length in the range of about 1 centimeter to about 10 centimeters. In such implementations, the braided electrode also has a length in the range of about 1 centimeter to about 10 centimeters. The braided electrode aperture also has a width in the range of about 60 degrees to about 180 degrees. Moreover, the braided electrode aperture may be oriented at various circumferential locations of the shaft. In one implementation, the braided electrode generally defines an electrode surface that is recessed below the level of the outer surface of the catheter shaft. Alternatively, the at least one braided electrode generally defines an electrode surface that is generally flush with the outer surface of the catheter shaft. In yet another alternative, the at least one braided shaft generally defines an electrode surface that is raised above the outer surface of the catheter shaft.

Generally, the braided electrode is configured to at least partially contact the tissue during use, although there may be instances when such contact does not occur. As such, the tissue is ablated by at least convection. The ablation catheter may also ablate the target tissue by conduction.

In some implementations, the catheter shaft may also define a second lumen. In such implementations, a control wire is connected with the catheter shaft and located within the second lumen. The control wire may be precurved to manipulate the catheter shaft such that the catheter shaft forms a substantially circular shape. For ablation procedures in the pulmonary vein, the substantially circular shape is adapted to conform to the inner shape of the pulmonary vein. The braided is connected with at least one corresponding wire adapted to connect with an ablation energy source. The wire is routed through the second lumen. However, the wire may be positioned in other locations, such as in the shaft wall.

In some particular implementations, the ablation catheter comprises at least a first braided electrode and a second braided electrode, wherein the first braided electrode and the second braided electrode are each separately connected to at least one ablation energy source. Additional braided electrodes may also be provided in the ablation catheter.

The present invention also involves a method of manufacturing an ablation catheter, and in one form, comprises the operations of obtaining a first shaft defining a first outside diameter; obtaining a second shaft defining a first inside diameter greater than the first outside diameter of the first shaft; and, obtaining at least one braided electrode. After obtaining the catheter components, the method involves placing the first shaft over a mandrel; placing the at least one braided electrode over the first shaft; and placing the second shaft over the at least one braided electrode.

The present invention also involves a method of ablating, and in one form, comprises the operations of locating an ablation catheter adjacent a tissue to be ablated wherein the ablation catheter defines a plurality of braided electrodes wherein each electrode is separately connected with a power supply; and separately energizing each braided electrode to ablate the tissue. During the ablation procedure, fluid may be guided past the braided electrode. The ablation catheter is placed in at least partial contact with the tissue.

A more detailed explanation of the invention is provided in the following description and claims, and is illustrated in the accompanying drawings.

DETAILED DESCRIPTION OF PREFERRED EMBODIMENTS

The present invention involves an ablation catheter employing an electrode with multiple conductive distributed strands arranged to distribute and deliver ablation energy to a target tissue. In one particular arrangement, the ablation catheter includes an electrode with multiple conductive strands configured in an interconnected braid or mesh-like pattern. Hereafter, an electrode including a plurality of wires or other energy conveying strands arranged in a weave, arranged in an overlapping, mesh-like, or spiral winding-like pattern, or configured in other braid-like patterns will be referred to as a "braided electrode." Once in place within the heart or in the proximity of the target tissue, the braided electrode may be pressed against or located in close proximity to the target tissue to convey energy to the target tissue to create a lesion. Hereafter, the term "ablation energy" will be used to refer to any energy source used to oblate tissue, such as radio frequency (RF), direct current, alternating current, microwave, and ultrasound.

In some embodiments, the ablation catheter may define a lumen or include a conduit of another form to convey a fluid material to and around the braided electrode during an ablation procedure. This fluid material can wash blood away from the braided electrode to help prevent the formation of coagulum, can cool the ablation electrode, and can convey ablation energy to the target tissue.

Figure 2:
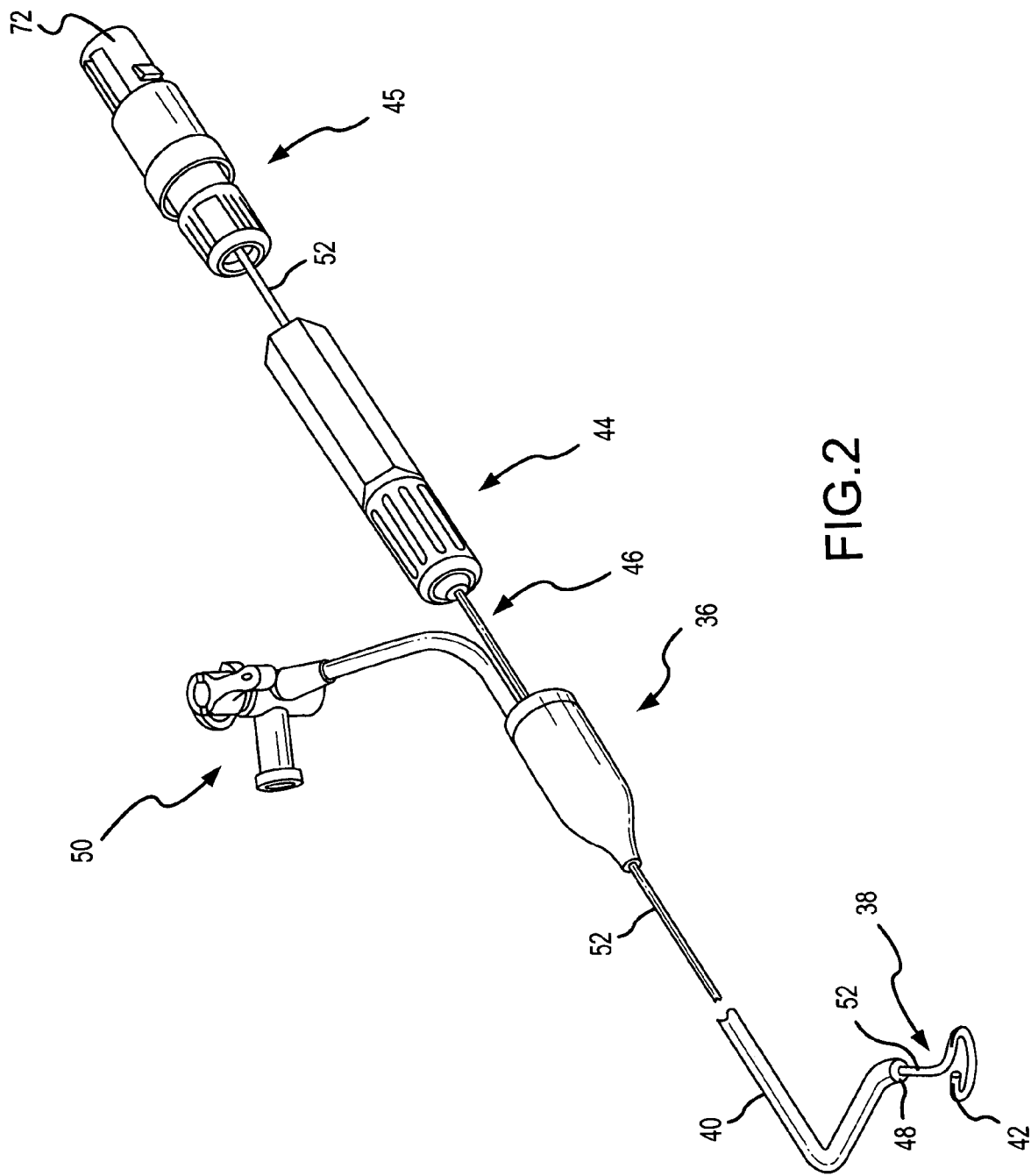
FIG. 2 is an isometric view of one embodiment of an ablation catheter assembly according to the present invention.

FIG. 2 illustrates one embodiment of a catheter ablation system 36 with an ablation catheter 38 extending from the distal end portion of a sheath 40 of a distal region of a guiding introducer. As used herein and commonly used in the art, the term "distal" is used generally to refer to components of the ablation catheter system, such as the braided electrode 42, that are located or generally orientated toward the heart or other target tissue when the ablation catheter is in use. On the other hand, the term "proximal" is used generally to refer to components or portions of the ablation catheter, such as a control handle 44 and a connector 45, that are located or generally orientated away from or opposite the heart or other target tissue when the ablation catheter is in use. The proximal end portion 46 of the shaft 52 of the ablation catheter 38 are operably associated with the control handle, which may be used by the physician to control various portions of the ablation catheter system during a procedure.

The sheath 40 is a tubular structure defining at least one lumen 48 or longitudinal channel. In one implementation, the sheath is fabricated with a flexible resilient material. The sheath, shaft, and other components of the ablation catheter system are preferably fabricated of materials suitable for use in humans, such as nonconductive polymers. Suitable polymers include those well known in the art such as polyurethanes, polyether-block amides, polyolefins, nylons, polytetrafluoroethylene, polyvinylidene fluoride, and fluorinated ethylene propylene polymers, and other conventional materials. The lumen of the sheath is configured to receive and guide the ablation catheter within the lumen to the appropriate location in the heart once the sheath is pre-positioned in the appropriate location.

To pre-position the sheath 40 at the appropriate location in the heart, a dilator and a needle (not shown) are fitted within the lumen 48 of the sheath. When the dilator and needle are within the lumen, the ablation catheter 38 is not within the lumen. In an example of an ablation procedure within the left atrium 18, the sheath and the dilator are first inserted in the femoral vein in the right leg. The sheath and dilator are then maneuvered up to the inferior vena cava 22 and into the right atrium 14. In what is typically referred to as a transseptal approach, the needle is pressed through the interatrial septum 24 between the right and left atria. Following the needle, the dilator is pressed through the small opening made by the needle. The dilator expands the opening sufficiently so that the sheath may then be pressed through the opening to gain access to the left atrium 18 and the pulmonary veins 32. With the sheath in position, the dilator is removed and the ablation catheter 38 is fed into the sheath 40 and pushed within the sheath into the left atrium 14. In some implementations, the sheath, dilator, and ablation catheter are each about two to four feet long, so that they may extend from the left atrium through the body and out of the femoral vein in the right leg and be connected with various catheter ablation procedure devices such as the control handle 44, one or more fluid control valves (not shown), and the like. A more detailed description of the process of forming an ablation at the left superior pulmonary vein is discussed below with regard to FIGS. 12 and 13. The ablation catheter system 36 is typically discussed herein with reference to procedures in the left atrium 18 in the vicinity of or within the pulmonary veins 32.

The ablation catheter system, however, is not limited to such procedures, and may be used for ablation of target tissue in other areas of the heart and body.

Figure 3A:
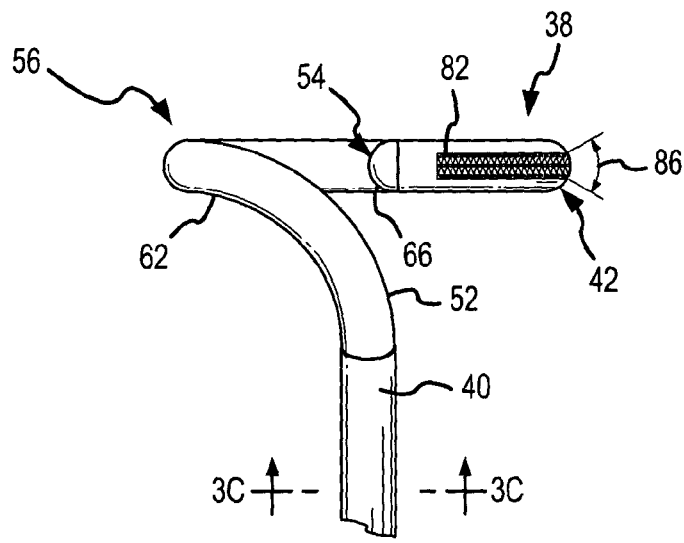
FIG. 3A is a front fragmentary view of the distal portion of one embodiment of an ablation catheter according to the present invention, the view of the ablation catheter looking perpendicular to the longitudinal axis of the sheath comprising a part of the ablation catheter assembly.
Figure 3B:
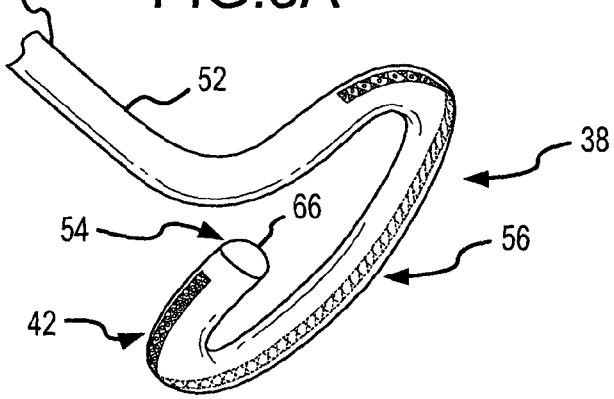
FIG. 3B is an isometric fragmentary view of the ablation catheter shown in FIG. 3A.
Figure 3C:
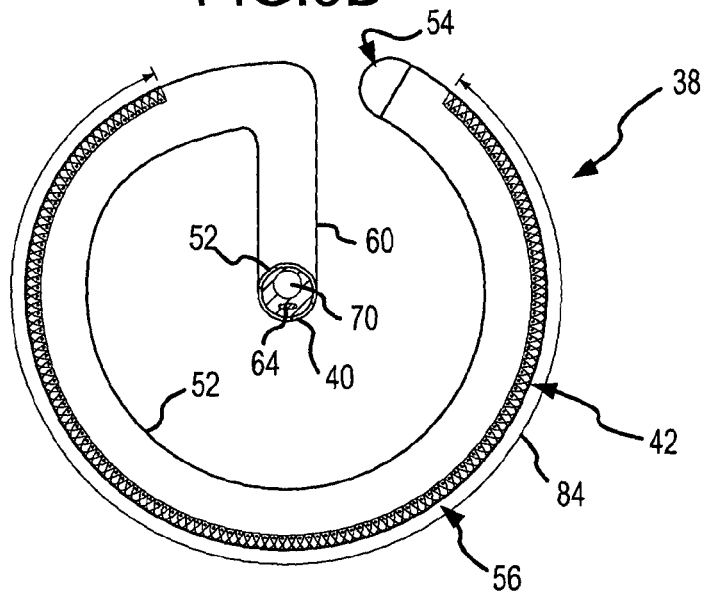
FIG. 3C is a fragmentary view taken along line 3C-3C of FIG. 3A, the view of the ablation catheter looking down the longitudinal axis of the sheath.
Figure 4A:
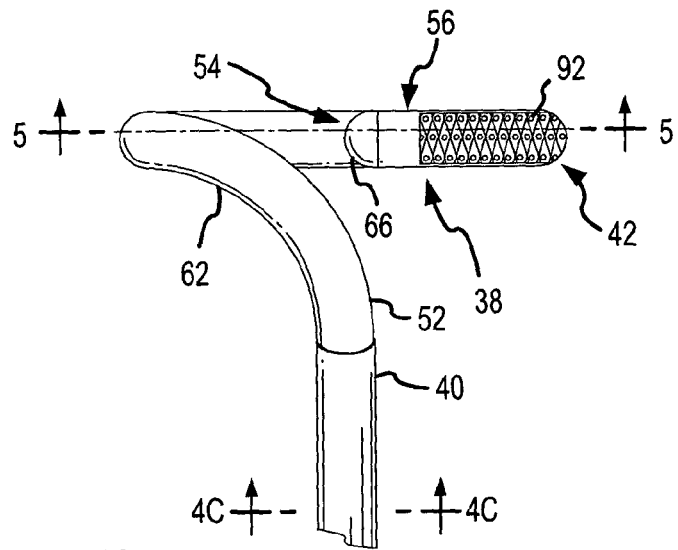
FIG. 4A is a front fragmentary view of the distal portion of another embodiment of an ablation catheter according to the present invention, the view of the ablation catheter looking perpendicular to the longitudinal axis of the sheath comprising a part of the ablation catheter assembly.
Figure 4B:
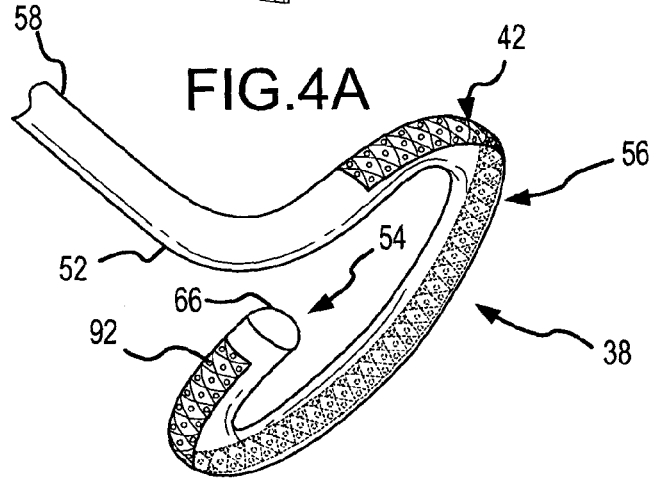
FIG. 4B is an isometric fragmentary view of the ablation catheter shown in FIG. 4A.
Figure 4C:
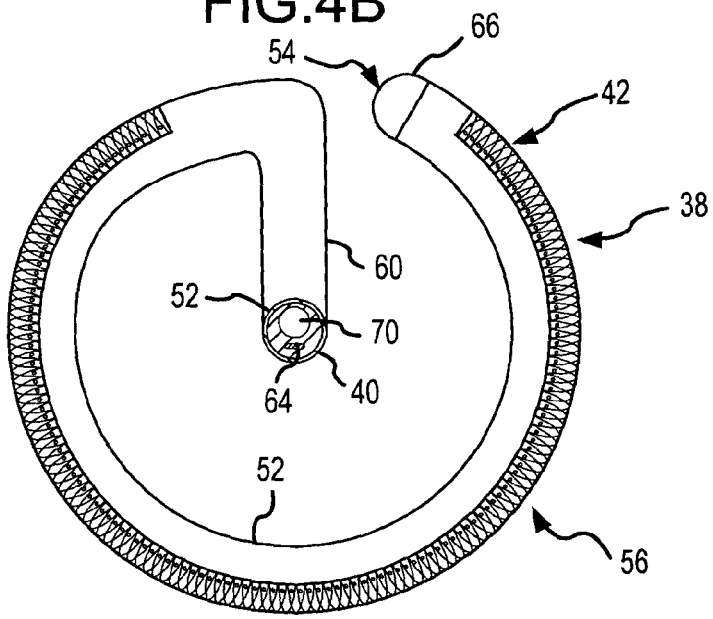
FIG. 4C is a fragmentary view taken along line 4C-4C of FIG. 4A, the view of the ablation catheter looking perpendicular to the longitudinal axis of the sheath comprising a part of the ablation catheter.

FIGS. 3A-3C illustrate one embodiment of the ablation catheter 38. FIGS. 4A-4C illustrate an alternative embodiment of the ablation catheter 38. Referring to both FIGS. 3A-3C and FIGS. 4A-4C, the ablation catheter includes the shaft 52 and the braided electrode 42. The braided electrode is positioned in proximity to the distal end of the ablation catheter. Some embodiments of the ablation catheter also contain one or a plurality of radiopaque tip marker bands (not shown) near the distal end. Alternatively, the tip markers may be located in other structures, such as in the distal end region of the sheath. The radiopaque tip markers allow the physician to track the location of the ablation catheter traveling within the body through radiopacity. As with the sheath 40, the shaft 52 of the ablation catheter is a flexible and resilient tubular structure with at least one lumen or conduit defined therein. In the examples shown in the various figures herein, the shaft defines a loop portion 56 housing the braided electrode. The looped shape of the shaft and the electrode housed therein facilitates formation of a circumferential lesion within one or more of the pulmonary veins or within the left atrium at the ostium to one or more of the pulmonary veins.

Figure 3D:
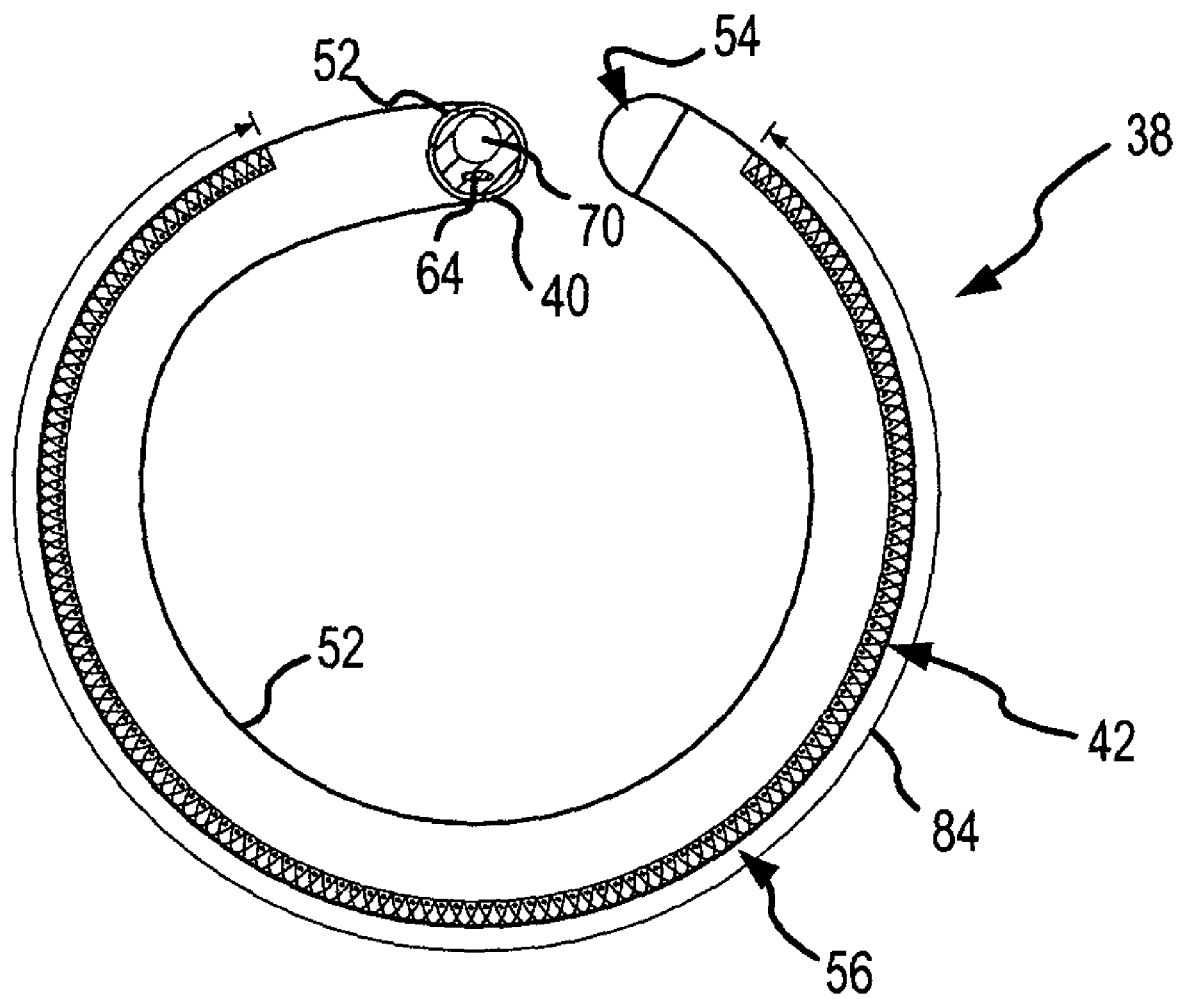
FIG. 3D is a representative fragmentary section view of an alternative ablation catheter with the loop offset from the longitudinal axis of the shaft.

In the embodiments shown in FIGS. 3A-3C and 4A-4C, the shaft 52 is precurved in such a manner to facilitate ablation within one of the pulmonary veins. As such, the precurved shape defines a first region 58 that is generally coaxially aligned with the distal end region of the sheath 40. The curved regions of the proximal end of the ablation catheter may be fabricated with a bonded polymer. The section of the shaft extending between the proximal end region and the curved region may be a braided catheter shaft. Following the first region is a second region 60. As best illustrated in FIGS. 3C and 4C, the second curved region 60 is adapted to position the loop region 56 so that the point generally defining the center of the loop is aligned with the longitudinal axis of the distal end region of the sheath 40. Note, FIG. 3D illustrates an embodiment of the ablation catheter similar to FIGS. 3A-3C; however, the center of the loop is offset from the longitudinal axis of the distal end region of the sheath. The loop portion 56 is shown in the figures as defining a generally circular-like, unclosed shape. The loop region, however, may form any closed or unclosed curved or generally arcuate shape, such as a circle or ellipse.

The shaft further defines a third curved region 62 following the second curved region. As best shown in FIGS. 3A and 4A, the third curved region curves away from the second curved region 60 to position a plane defined by the loop 56 generally perpendicular to the longitudinal axis defined by the first region 58 and the distal end region of the guiding introducer or sheath 40.

Figure 5:
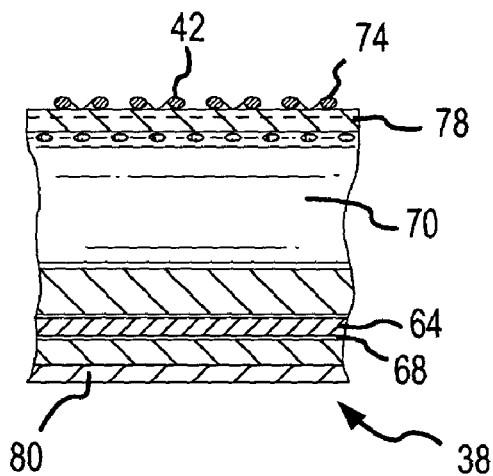
FIG. 5 is a section view taken along line 5-5 of FIG. 4A.
Figure 6:
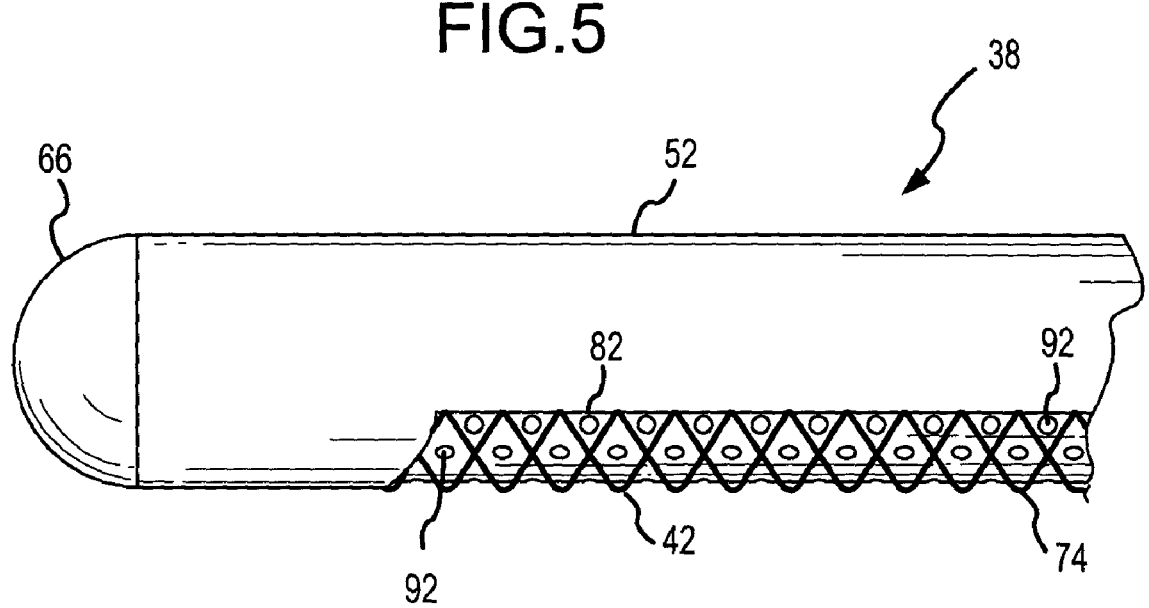
FIG. 6 is a representative partial top view of one uncurved or straight embodiment of an ablation catheter according to the present invention.
Figure 7:
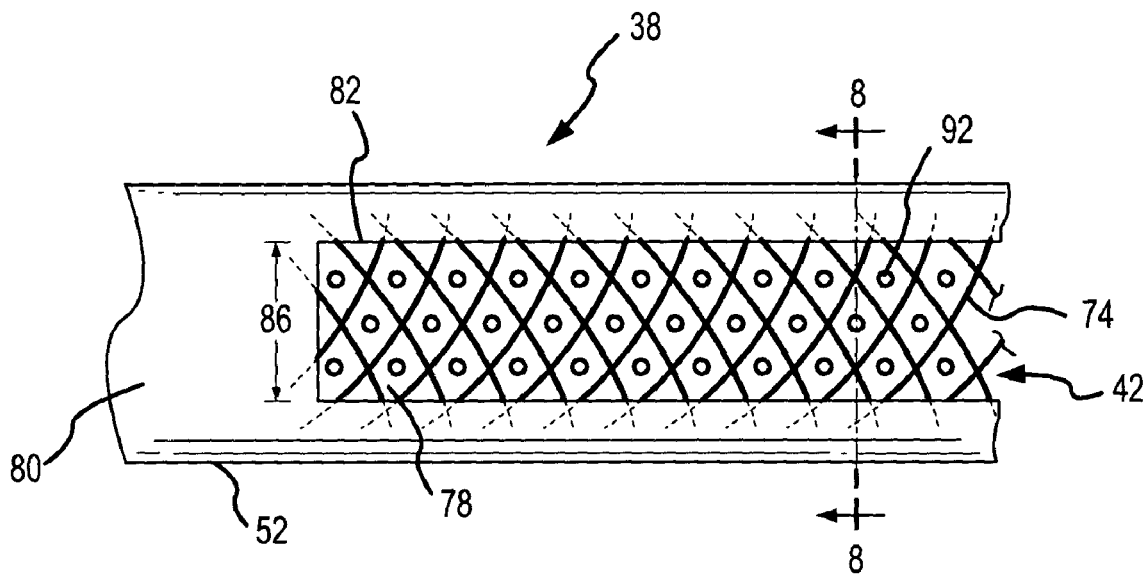
FIG. 7 is a representative partial side view of the embodiment of the ablation catheter shown in FIG. 6.
Figure 8:
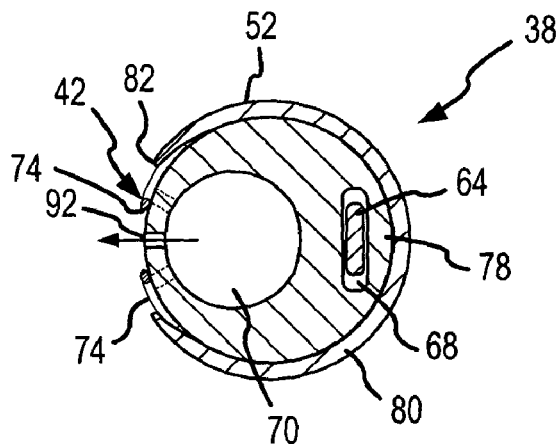
FIG. 8 is a cross-sectional view taken along line 8-8 of FIG. 7, the section view illustrating a fluid lumen, a control wire lumen with a control and shaping wire therein, and other features of an example of an ablation catheter according to the present invention.
Figure 10:
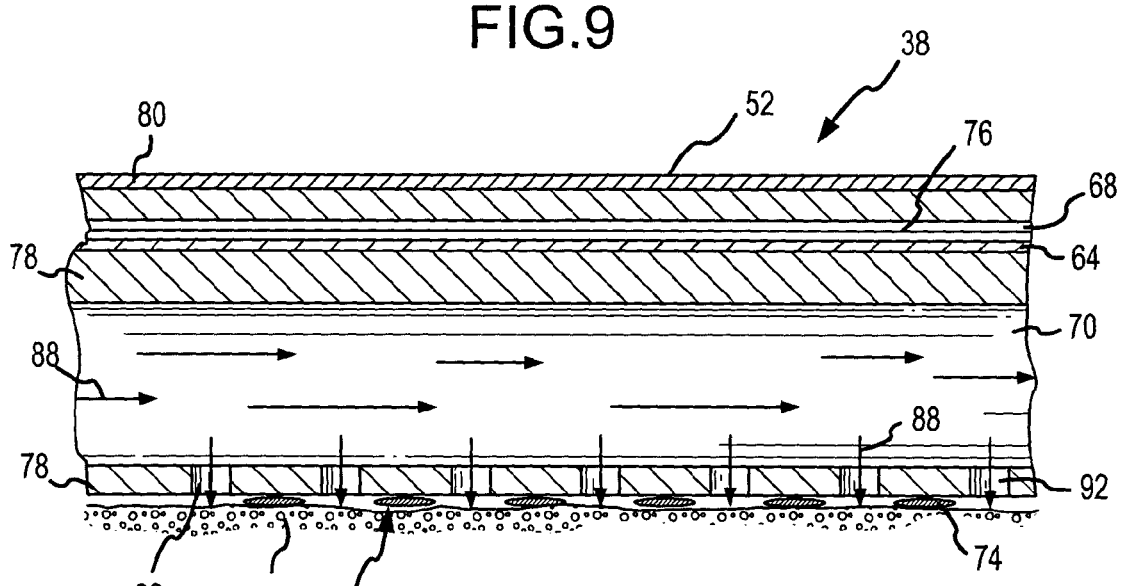
FIG. 10 is a representative partial top section view of an ablation catheter according to the present invention.

Instead of a precurved shaft, a straight shaft 52 as shown in FIGS. 5-8 may include a pull wire 64 within the shaft that causes the shaft to form the loop-shape or other desired curved shape, and is configured to modify the loop when the physician performing the procedure pulls on the pull wire. Alternatively, a curved shaft (shown in FIGS. 3A-4C and others) may be employed along with the pull wire 64 so that the physician performing the ablation procedure may change the size and shape of the curved shaft. In one implementation, the pull wire is secured to a tip 66 of the ablation catheter 38 or to a side of the shaft. Additionally, the control and shaping pull wire is housed within a wire lumen 68 defined within the shaft. The wire lumen 68 is best illustrated in FIGS. 5, 8, and 10.

In embodiments of the ablation catheter 38 that include a control or shaping wire 64, and either a precurved or uncurved shaft 52, the control or shaping wire may be fabricated of a super elastic metal alloy material, such as a nickel-titanium alloy. One such suitable nickel-titanium alloy is commonly referred to as Nitinol. A suitable super elastic material for the pull wire 64 is a shape memory alloy with a transformation temperature below that of the human body temperature. Alternatively, the shape memory alloy may also have a transformation temperature above that of the human body. In this alternative utilization, an electric current is applied to the shape memory alloy material to convert it into a super elastic state. When such a super elastic, shape memory alloy is utilized, the control or shaping wire may be precurved and it will retain its curvature to help guide the ablation catheter 38 or form the loop 56 of the ablation catheter when it is moved out of the sheath 40, while still retaining sufficient flexibility to support the ablation catheter as it is pressed against the target tissue. However, in some embodiments of the ablation catheter, the control wire 64 need not be precurved as the shaft will be precurved. In such instances, the control wire will be used to control the shape or circumference of the loop portion of the shaft so that it may be maneuvered into or adjacent different size veins.

As best shown in FIG. 8, which is a section view taken along line 8-8 of FIG. 7, in one embodiment, the cross-section of the control and shaping wire 64 is generally rectangular and is about 0.02 inch to about 0.07 inch in width and from about 0.005 inch to about 0.02 inch (about 0.01 centimeter to about 0.05 centimeter) in thickness. As the control wire is configured as a flattened wire, it is resistant to bending laterally while still retaining sufficient flexibility.

As shown in FIGS. 3A-C and 4A-C, the distal tip 66 is secured to the distal end of the shaft 52. The tip seals the end of a fluid lumen 70 (see also FIG. 5 and others) and the wire lumen 68. The distal tip may be a blunt end, may be an electrode configured to energize and ablate tissue, or may be a sensing electrode to provide mapping. In the event the tip is configured as an electrode, it will include a wire strung through the wire lumen or through the fluid lumen to a connector 72 at the proximal end region of the ablation catheter 38.

The loop-shaped region 56 of the shaft 52 houses the braided electrode 42 that is at least partially exposed along the outer circumference of the loop. Regardless of how the loop and the overall curved shape of the shaft is obtained, the overall precurved shape of the shaft is defined so that the loop portion may be directed toward one of the pulmonary veins such that the entirety of the electrode is placed in complete or partial circumferential contact with the wall of the target vein. When positioned as such, the braided electrode may be manipulated and energized to form a complete or nearly complete circumferential lesion adjacent to or within the pulmonary vein. Such a circumferential lesion in some instances can completely eliminate harmful signals from traveling in the heart through one of the pulmonary veins.

As shown in FIG. 7 and other figures, in some implementations, the braided electrode 42 defines a plurality of electrode strands 74 interconnected in a mesh-like pattern. The mesh-like pattern of electrically conductive strands defines a plurality of diamond-shaped areas therebetween. The braided electrode is connected to at least one wire 76 (shown in FIG. 10), such as with a solder joint, that is strung through the shaft. The proximal end of the wire (i.e., the end opposite the connection to the braided electrode) includes the connector 72 (shown in FIG. 2) that may be plugged into a power supply that provides ablation energy to the electrode 42. The ablation energy, in one example, is RF energy supplied from a 50 watt power supply. Each strand of the braided electrode is interconnected. Thus, when the ablation energy is supplied to the braided electrode 42 it radiates outwardly from each strand 74 toward the target tissue. As will be discussed in more detail below, in some implementations, a plurality of braided electrodes may be employed with each braided electrode having a separate connection to the power supply. In implementations with a second lumen, the wire may be routed to the proximal end of the oblation catheter through the second lumen.

Figure 9:
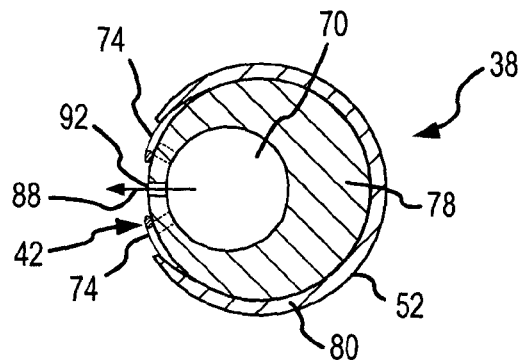
FIG. 9 is a representative section similar to the section view shown in FIG. 8, and not including the control wire lumen.

FIG. 5 is a partial section view of the loop region 56 of shaft 52 taken along line 5-5 of FIG. 4A. FIG. 8 is a section view taken along line 8-8 of FIG. 7, and FIG. 9 is a representative section view similar to that of FIG. 8 but without a control wire and control wire lumen. Referring to FIGS. 5-9 and other figures, the braided electrode 42 is secured within the ablation catheter 38 between an inner surface 78 and an outer surface 80. In one implementation the inner surface and the outer surface are both generally tubular, flexible, resilient structures with the diameters of the two tubular structures configured so that the outer surface will fit fairly tightly over the inner surface or be bonded to the inner surface. The braided electrode is formed into a partially or completely closed tubular structure and is sandwiched between the inner and outer surfaces. In one particular implementation, the inner surface of the shaft of the ablation catheter defines the fluid lumen 70 adapted to provide a flow path for a fluid material.

Figure 8A:
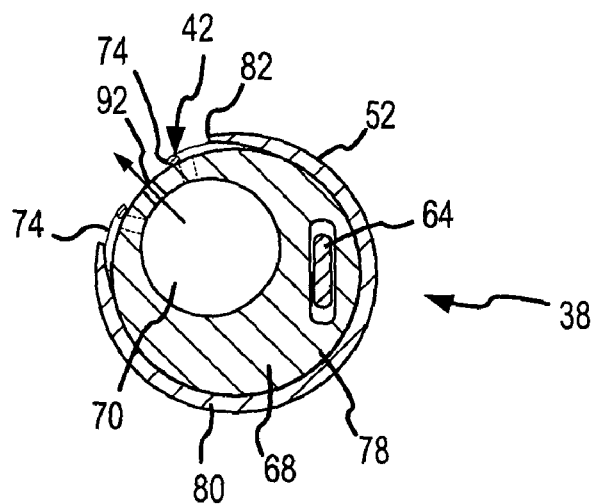
FIG. 8A is a representative section view similar to FIG. 8, but with the braid window and braided electrode oriented at a different location along the circumference of the catheter shaft.

The outer surface 80 of the shaft 52 is partially removed to define a braid window 82, which exposes at least a portion of the braided electrode 42. Alternatively, the outer surface may be fabricated to define an elongate rectangular aperture or braid window that is placed over the braided electrode during assembly so that the braided electrode is at least partially exposed. In some particular implementations, the braid window may be in the range of 1 centimeter to 10 centimeters in length (see FIG. 3C, ref. no. 84) along the circumference of the loop 56 and in the range of about 60 degrees to about 180 degrees in width (see FIG. 3A, ref. no. 86) along the circumference of the shaft 52. The braid window may also be arranged at various circumferential locations of the shaft. For example, FIG. 8A illustrates the braid window and braided electrode oriented slightly above that of FIG. 8. The braid window should be dimensioned so that a portion of the braided electrode remains sandwiched between the inner 78 and outer 80 surface to secure the electrode in place. Depending on the thickness of the braided electrode strands 74 and the thickness of the outer surface 80, the outer surface of the braided electrode may be slightly raised, lowered, or flush with the outer surface of the ablation catheter 38.

During an ablation procedure, it is important to prohibit, to the extent possible, the formation of coagulum or blood clots, which can be dangerous to the patient. Coagulum is produced when blood is heated to a temperature of about 70 degrees Celsius or higher. In some instances, coagulum is accompanied by emboli that can also be dangerous to the patient. As shown in FIG. 10 and others, in some particular configurations, the fluid lumen 70 is used to guide a fluid material to and around the braided electrode strands 74 to remove blood therefrom and to help reduce the formation of coagulum. In addition, when conductive fluids, such as hypertonic saline, are used, the fluid material can both cool the electrodes and transfer ablation energy between the electrodes and the tissue 90 to facilitate the ablation. Moreover, the presence of cooling fluid flowing over and around the braided electrode 42 allows greater energy to be applied to the tissue contacting or proximate the electrode strands. However, because the braided electrode may be pressed directly against the target tissue, little direct ablation temperature is lost due to the saline.

The fluid lumen 70 is fluidly connected with the fluid connector and control valve 50 (shown in FIG. 2). The fluid connector and control valve supplies fluid to the fluid lumen and controls the volume and velocity of the fluid therein. To guide the fluid material past the electrodes and toward the target tissue, a plurality of apertures 92 or ports are defined in the inner surface 78 between the fluid lumen 70 and the braided electrode 42. In one implementation, the apertures are drilled or otherwise formed in the inner surface between the braided strands of the electrode and within the braid window 82 in the outer surface 80. Thus, fluid 88 flowing within the fluid lumen is guided out of the ports and around the strands. The ports may define any shape, and in one implementation are generally circular. Furthermore, the ports may define any size. Generally, the size of the fluid apertures is dependent, in part, on the number of apertures, the pressure, velocity, the desired volume of fluid flowing within the fluid lumen, the distribution of apertures, the shape of the apertures.

In one particular implementation, the apertures 92 are located to guide the fluid material 88 through the diamond shaped areas defined by the intersection of the braided strands 74. In addition, the apertures are of a diameter less than the area bounded by the strands defining the diamond-shaped braided regions. The ablation energy will be distributed across the numerous strands of the braided electrode. As such, the ablation energy will be less concentrated at any particular electrode, such as in some conventional ring electrodes. To adequately cool the electrodes and wash blood away from the electrodes, numerous small holes may be used to convey fluid past and around the electrodes. Variable fluid flow past the electrodes can result in localized hot spots and formation of coagulum. The ability to employ small size ports 92 allows fluid to be distributed more evenly across the length of the braided electrode 42 even given the arcuate shape of the fluid lumen 70 conveying the fluid to the braided electrodes. Such even distribution can help to reduce the formation of hot spots. Additionally, modification of the loop 56 shape and thus the fluid lumen 70 during a procedure will result in little or no distortion of the port 92 shape and thus will have little or no impact on fluid flow along the length of the braided section. Although larger holes may be employed, they may result in unevenness in fluid distribution when the shaft 52 is looped as the fluid will tend to exit in greater volume through the holes along the curve nearer the proximal end of the shaft.

Figure 11:
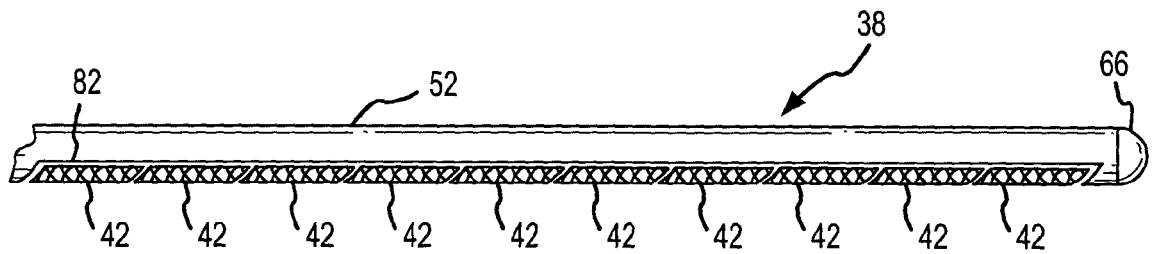
FIG. 11 is a top view of a straight ablation catheter employing a plurality of separately energized braided electrodes according to the present invention.

FIG. 11 is a perspective view of an ablation catheter 38 employing multiple braided electrodes 42 that are each independently connected with a power supply. In one particular implementation, each braided electrode is about 1 centimeter long, and each braided electrode is connected to a fifty watt generator through a switch or other device that allows power from the generator to be delivered to each braided electrode in sequence. Fifty watt generators are commonly found in surgical facilities and are capable of supplying adequate ablation energy to about a one centimeter braided electrode. Longer electrodes may require a higher power generator. Some of the pulmonary veins can define an inner circumference that is about 10 centimeters in length. To ablate a circumferential lesion around the entire internal circumference of a pulmonary vein, the ablation catheter shown in FIG. 11 may be positioned within the target pulmonary vein and the braided electrodes powered sequentially or generally intermittently to form a continuous lesion around the entire internal circumference of the target vein. Thus, by employing multiple electrodes, the ablation catheter may be positioned once and then held in place as each braided electrode is energized until the ablation is complete. Once positioned, such a procedure might take about ten minutes and not require any repositioning of the catheter.

Some embodiments of the ablation catheter discussed herein may be manufactured using conventional techniques. Alternatively, the single braided electrode and multiple braided electrode ablation catheter embodiments illustrated herein may be manufactured in accordance with the following method. First, the inner surface 78 of the shaft 52 and the outer surface 80 of the shaft are separately extruded. Next, the inner surface of the shaft is placed over a mandrel. Once in position on the mandrel, the one or more braided electrodes 42 are positioned in the appropriate location over the inner surface. If multiple electrodes are used, then each electrode is positioned so as not to contact an adjacent electrode to keep the electrodes electrically isolated from each other. After positioning the electrodes, the outer surface is placed over the braided electrode and the inner surface, and a shrink tube is employed to bond the inner surface to the outer surface. The power wires may be connected with the braided electrode and routed to the connector using conventional techniques. Moreover, the distal tip 66 may be secured to the shaft using conventional techniques.

This method of manufacture allows different shaft material to be used and different braid patterns to be used. Along the length of the shaft various stiffness materials may be employed to provide variability of the overall stiffness of the shaft along its length. For example, at the proximal end of the shaft, a relatively stiff material might be employed to shaft, assist in inserting and pressing the shaft through the sheath. Whereas, at the distal end of the shaft, a relatively soft material may be employed to provide greater flexibility and ease of maneuverability to position the ablation catheter.

Figure 1:
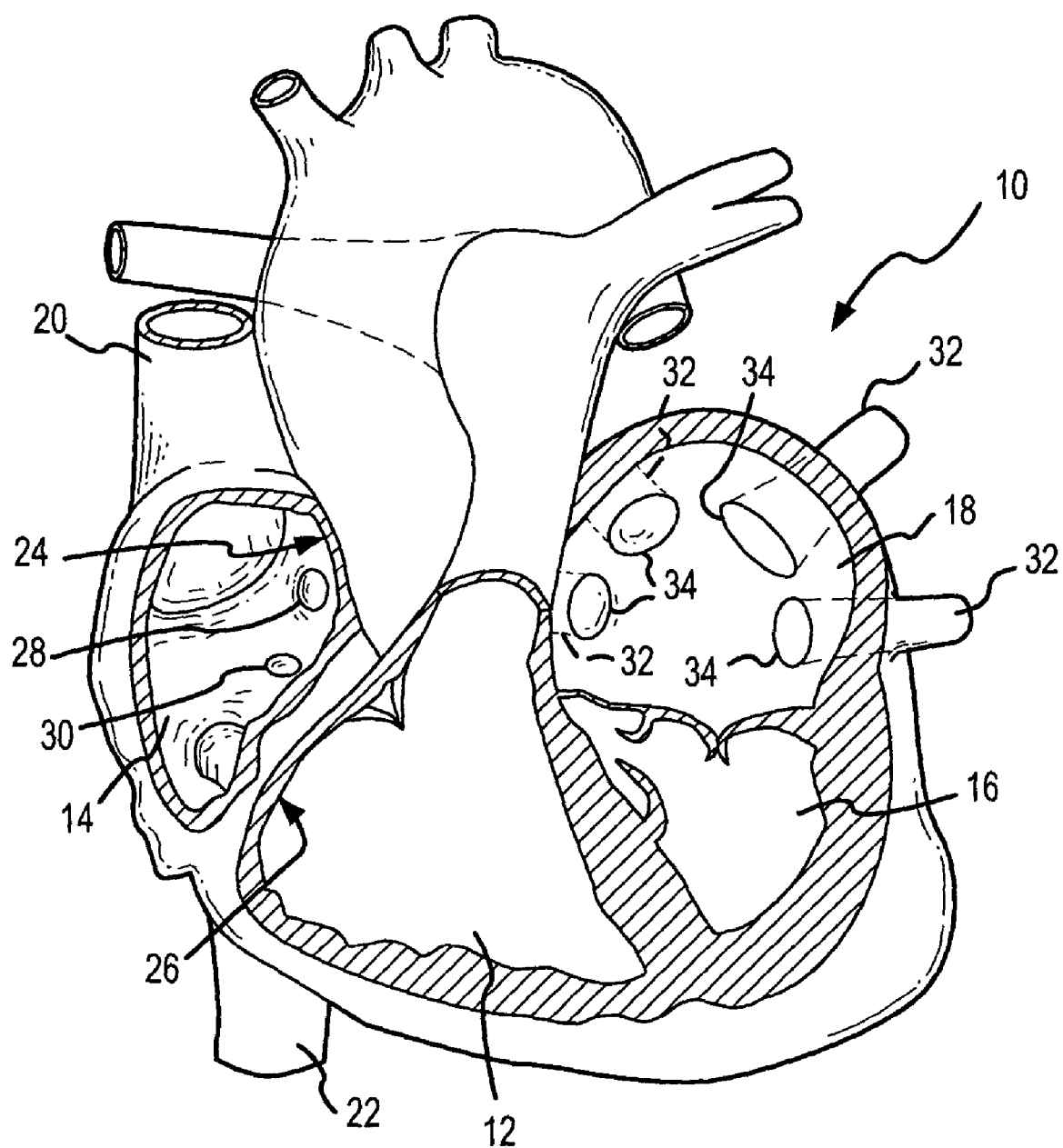
FIG. 1 is a partial cut away diagram of a human heart.
Figure 12:
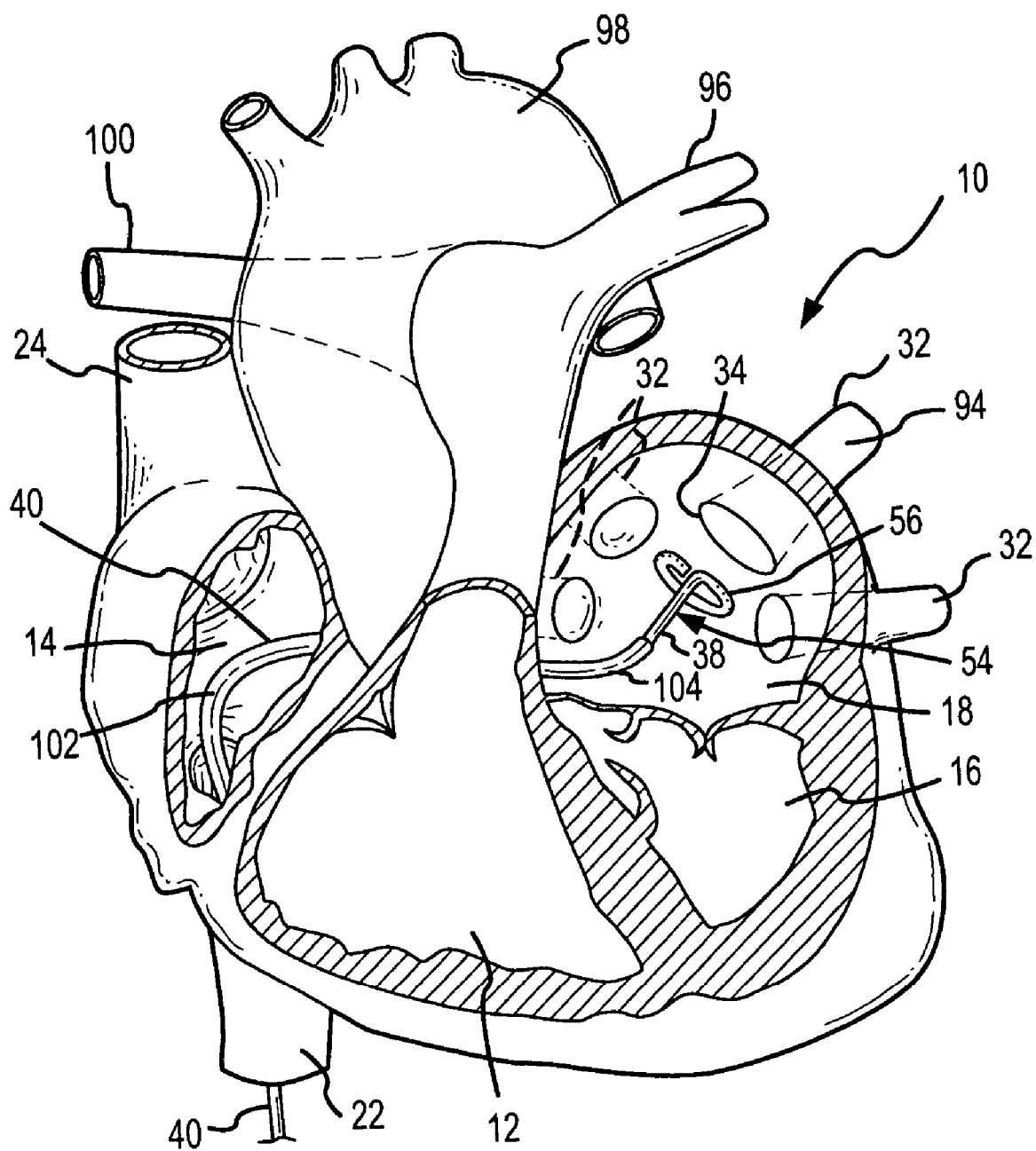
FIG. 12 is a partial cut away diagram of the human heart showing a sheath routed from the inferior vena cava, into the right atrium, through the interatrial septum, and into the left atrium, and with an ablation catheter extending outwardly from the sheath in alignment with the left superior pulmonary vein.
Figure 13:
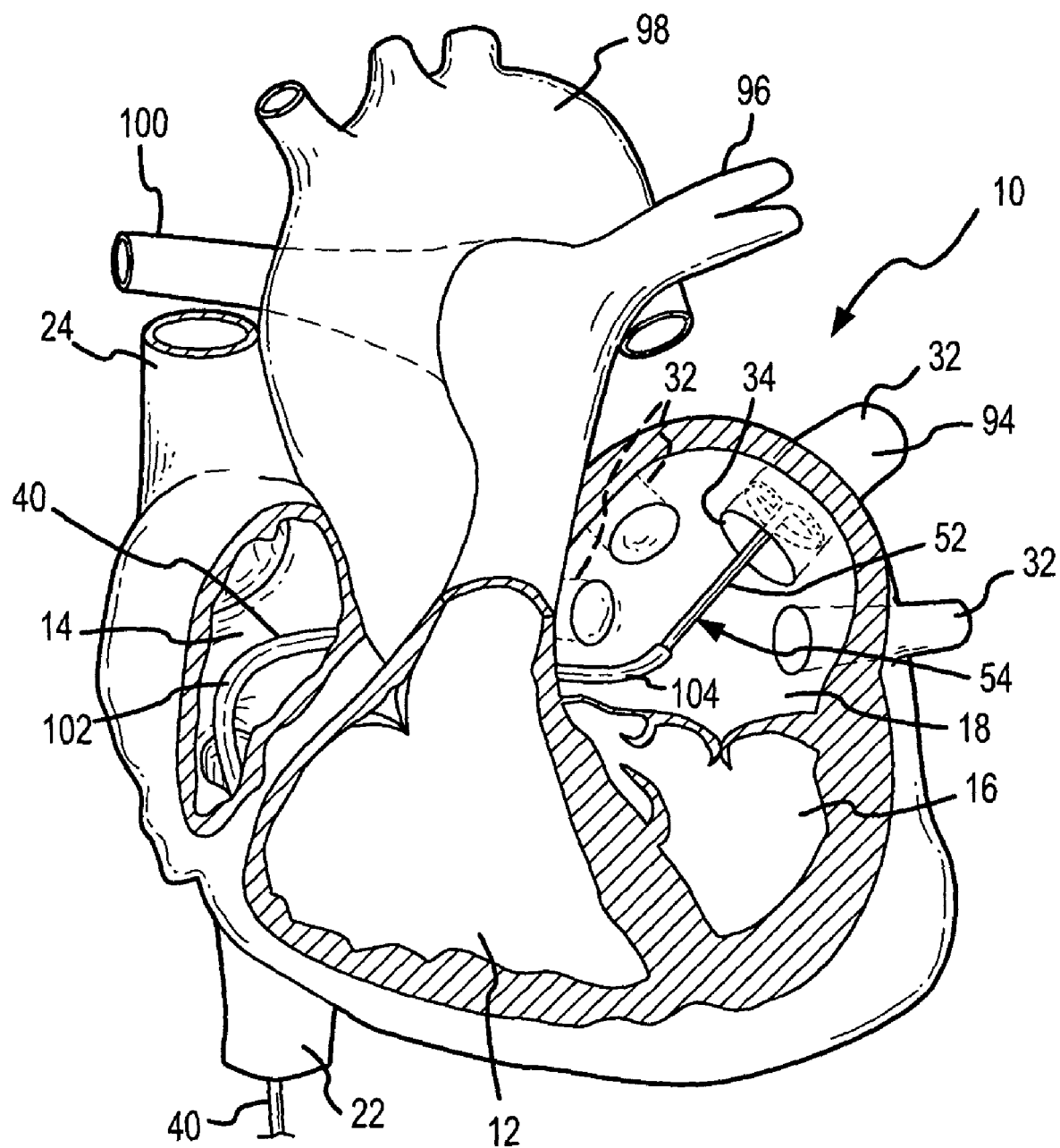
FIG. 13 is a partial cut away diagram of the human heart showing a sheath routed from the inferior vena cava, into the right atrium, through the septum, and into the left atrium, and with an ablation catheter extending into the left superior pulmonary vein to form an ablation therein.

FIGS. 12 and 13 depict the ablation catheter according to the present invention while being used to ablate tissue in the left superior pulmonary vein 94. FIGS. 12 and 13 include a number of primary components of the heart (also shown in FIG. 1) to orient the viewer. In particular, starting in the upper left hand portion of FIGS. 12 and 13 and working around the periphery of the heart in a counterclockwise fashion, the following parts of the heart 10 are depicted: superior vena cava 24, right atrium 14, inferior vena cava 22, right ventricle 12, left ventricle 16, left superior pulmonary vein 94, left atrium 18, left pulmonary artery 96, arch of aorta 98, and right pulmonary artery 100. The distal portion 54 of the ablation catheter is positioned adjacent to the ostium 34 of the left superior pulmonary vein 94. For example, to get the distal portion 54 of the ablation catheter 38 in the position shown in FIG. 12, the right venous system may be first accessed using the "Seldinger technique," wherein a peripheral vein (such as a femoral vein) is punctured with a needle, the puncture wound is dilated with a dilator to a size sufficient to accommodate the sheath. The sheath with at least one hemostatic valve is seated within the dilated puncture wound while maintaining relative hemostasis. The sheath with a dilator and needle housed within the lumen are advanced along the peripheral vein, into the region of the vena cava (e.g., the inferior vena cava 22), and into the right atrium 14. From there, the sheath 40 is further advanced through a hole in the interatrial septum, which a doctor would make using the needle and dilator. Once the sheath is fit through the interatrial septum and gains access to the left atrium 18, the sheath is positioned generally along the longitudinal axis of one of the pulmonary veins. In FIG. 12, the sheath is shown in alignment with the longitudinal axis of the left superior pulmonary vein 94. Positioned as such, the dilator and needle are pulled back through the sheath.

To facilitate the proper positioning of the sheath within the left atrium, in one particular implementation, the sheath is preset with a curvature defined to assist in maneuvering the sheath to the correct position within the heart. The curvature will depend on the location within the heart in which the catheter will be guided for the ablation procedure. In the example of an ablation procedure within the left atrium 18 and in proximity or within one of the pulmonary veins 32, the sheath is preset with a complex three dimensional curve with a first section 102 corresponding with the turn between the inferior vena cava 22 toward the septum and with a second section 104 corresponding with the curve between the septum and one of the pulmonary veins. The curve in the sheath may be set by heating up the sheath on a die. The die defines the desired curvature, and heating the sheath on the die sets the curve in the sheath.

To properly guide the ablation catheter 38 to the appropriate location, other guiding systems may be employed, such as precurved guiding introducers and the like. For example, the ablation catheter may be properly guided within the heart with a guiding introducer system including one or more guiding introducers and a rail and ablation catheter system as described in U.S. Pat. No. 6,120,500, titled "Rail Catheter Ablation and Mapping System," which is hereby incorporated by reference in its entirety as though fully set forth herein. In another example, the ablation catheter may be properly guided within the heart using a guidewire such as is described in U.S. Pat. No. 5,162,911, titled "Over-the-wire catheter," which is hereby incorporated by reference it its entirety as though fully set forth herein.

After the sheath 40 is properly positioned and the dilator is removed, the ablation catheter 38 is fed through the lumen 48 at the proximal end of the sheath and out the distal end of the sheath. In an embodiment of the ablation catheter that is precurved to provide a looped area 56, upon exiting the sheath 40 the ablation catheter assumes its precurved shape. As shown in FIG. 12, the plane defined by the looped portion of the shaft will be generally perpendicular to the longitudinal axis of the target pulmonary vein after the shaft exits the sheath.

Figure 14:
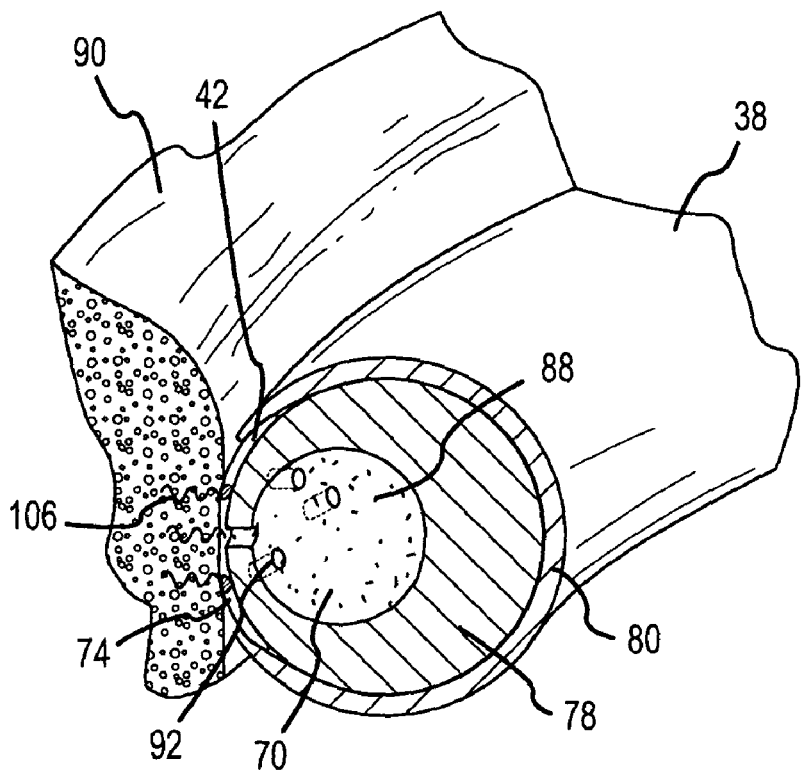
FIG. 14 is a close-up partial isometric section view of the loop portion of the ablation catheter positioned against target tissue so that the braided electrode is completely or partially in contact with the target tissue and illustrating the ports between the fluid lumen and the braided electrode.
Figure 15:
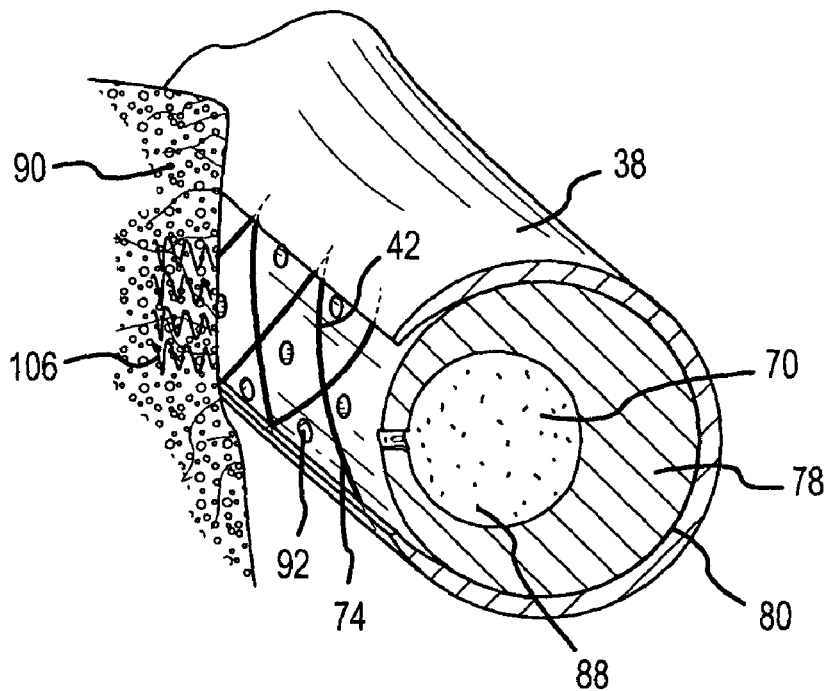
FIG. 15 is a close-up partial isometric section view of the loop portion similar to that of FIG. 14, but viewing the shaft more from the side of the braided electrode.
Figure 16B:
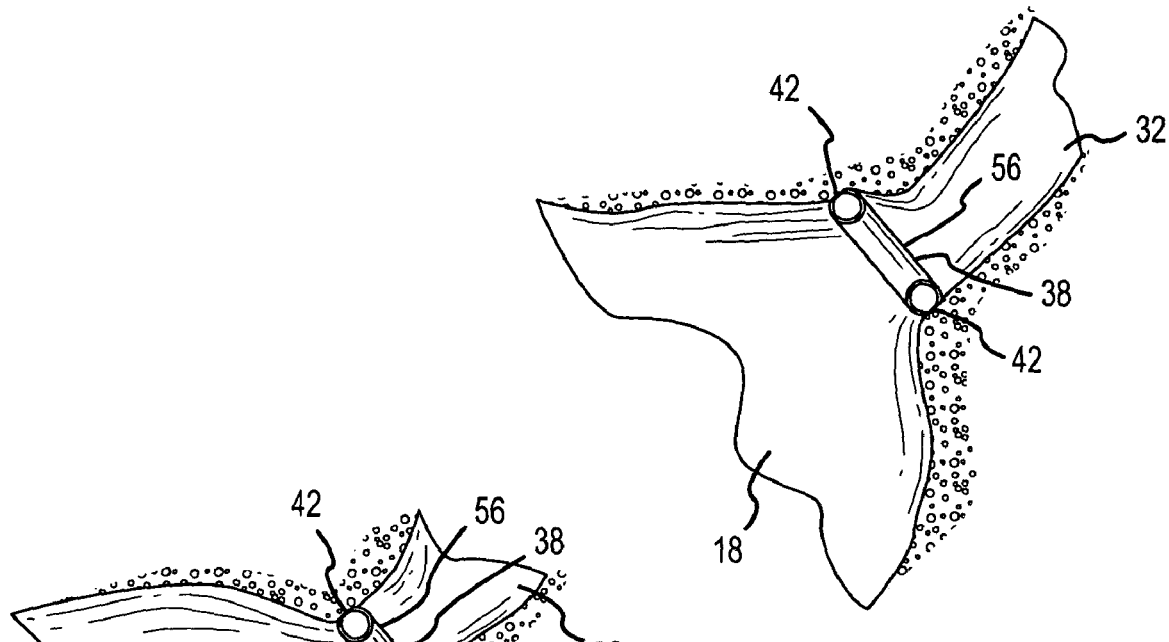
FIG. 16B is a representative section view of the looped portion of the ablation catheter and braided electrode positioned partially against the wall of the pulmonary vein and partially against the ostium to the pulmonary vein.
Figure 16A:
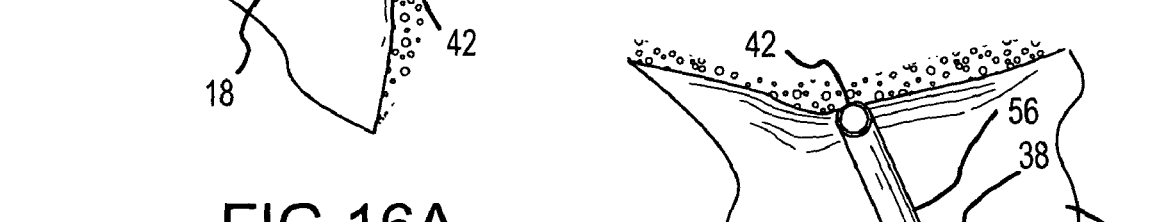
FIG. 16A is a representative section view of the looped portion of the ablation catheter and braided electrode pressed against the walls of the pulmonary vein.
Figure 16D:
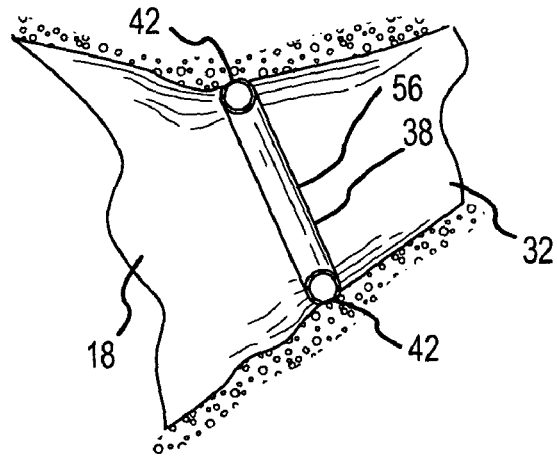
FIG. 16D is a representative section view of the looped portion of the ablation catheter and braided electrode pressed against the walls of a pulmonary vein adjacent a relatively large ostium thereto.
Figure 16C:
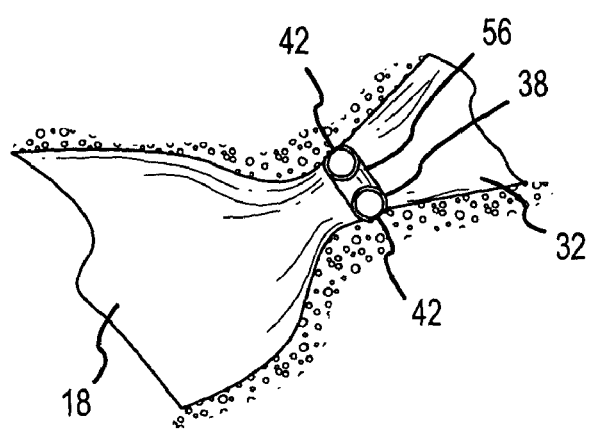
FIG. 16C is a representative section view of the looped portion of the ablation catheter and ablation electrode pressed against a somewhat conically shaped wall of the pulmonary vein.

In FIG. 13, the distal looped portion 56 of the ablation catheter 38 has been inserted into the left superior pulmonary vein 94. While the ablation catheter is in the pulmonary vein as depicted in FIG. 13, the braided electrode 42 would be activated to create the desired lesion in the left superior pulmonary vein. FIGS. 14 and 15 are partial isometric section views of the ablation catheter 38 illustrating the braided electrode 42 in contact with the target tissue 90. As shown in FIGS. 14 and 15, the RF energy 106 emanating from the braided electrode passes into the target tissue to heat the tissue through ohmic and conductive heating. In addition, RF energy also passes through the conductive medium 88 flowing out the ports 92 and past the electrode strands 74 and into the target tissue. The conductive medium experiences ohmic heating as it flows past the braided electrode. Thus, a lesion is formed in the target tissue not only by the braided electrode in contact with the target tissue, but also by the hot conductive medium flowing along the target tissue.

As mentioned above, in order to form a sufficient lesion, it is desirable to raise the temperature of the tissue to at least 50° C. for an appropriate length of time (e.g., one minute). Thus, sufficient RF energy 106 must be supplied to the braided electrode 42 to produce this temperature in the adjacent tissue for the desired duration. The conductive medium 88 flowing through the ports 92 prevents blood from flowing into the ablation catheter 38 and pushes blood from the area adjacent to the ports. This helps prevent coagulum, which can have undesirable effects on the patient. The conductive medium is also caused to flow at a rate that prevents the electrode from overheating the conductive medium producing vapor in the fluid lumen 70. If the conductive medium were to boil, for example, creating a vapor, the ablation catheter's ability to form a desired lesion in adjacent tissue would be reduced since less RF energy would be able to reach the tissue. Thus, the flow of conductive medium through the fluid lumen and out the ports is managed or regulated so that there is sufficient flow to prevent vaporization, but not so much flow that the braided electrode 42 is prohibited from sufficiently heating the adjacent tissue to form a desired lesion. Also, if too much conductive medium flows out of the ports 92, the hemodynamics of the patient may be adversely affected by the excess quantity of conductive medium being mixed with the patient's blood. The desired flow rate is achieved by adjusting the pressure or volume rate driving the conductive medium through the fluid lumen, the diameter of the ports, and the spacing between the ports. Another factor that may be taken into account when adjusting the flow rate of the conductive medium is the specific configuration of the distal portion 54 of the ablation catheter since the flow of conductive medium is somewhat affected by the curvature of the catheter shaft 52.

FIGS. 16A-16D are representative section views of the ablation catheter 38 positioned within or adjacent to one of the pulmonary veins 32. Collectively, these figures illustrate the flexible resilient nature of the ablation catheter, and the way it way be positioned to provide a circumferential lesion within differently shaped veins or within differently shaped portions of veins. Such shapes may be achieved with a curved or partially curved ablation catheter shaft 52 with or without the assistance of a control and shaping wire 64. Straight ablation catheter shafts would require a control and shaping wire or other device to achieve a loop shape.

In the example of an ablation catheter that includes a partially precurved shaft 52 and a control wire 64, upon exiting the sheath 40, the shaft forms a first loop shape 56. By pulling gently on the control wire, the loop may be contracted, i.e., the diameter of the loop lessened, so that the shaft and electrode may be extended into veins that have a smaller diameter than the shaft loop when it first exits the sheath. Once within the vein, the control and guidewire may be completely or partially released so that the shaft loop expands and presses the braided electrode 42 against the wall of the vein. To retract the ablation catheter, the control wire would again be gently pulled to tighten the loop and pull the ablation catheter out of the vein.

As also shown in FIGS. 16A-16D, by providing the ablation electrode in a window 82 that is from 60 degrees to about 180 degrees (86), when the loop is expanded against a vein, it may contact the vein at different points along the outer radius of the shaft and still contact the braided electrode. Thus, in some places, the braided electrode may contact the tissue along the top portion of the braided electrode and in other places the braided electrode may contact the tissue along the bottom portion of the braided electrode.

Although preferred embodiments of this invention have been described above with a certain degree of particularity, those skilled in the art could make numerous alterations to the disclosed embodiments without departing from the spirit or scope of this invention. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ablation catheter comprising:
a fixed braided electrode means for forming an ablation lesion through contact with a target tissue;
catheter shaft means for locating the braided electrode means adjacent the target tissue, the catheter shaft means including an inner tubular structure and an outer tubular structure; and
lumen means for channeling a fluid media through the braided electrode means,
wherein the fixed braided electrode means is sandwiched between the inner tubular structure and the outer tubular structure and extends around less than about 180 degrees of a circumference of the catheter shaft means.

2. The ablation catheter of claim 1 wherein:
the inner tubular structure of the catheter shaft means defines at least one fluid aperture providing a fluid flow path through the braided electrode means.

3. The ablation catheter of claim 2 further comprising:
an introduction system in fluid communication with the lumen means, the introduction system configured to provide a fluid media to the lumen means.

4. The ablation catheter of claim 3 wherein the lumen means is configured to guide the fluid media through the at least one fluid aperture.

5. The ablation catheter of claim 4 wherein the at least one fluid aperture is located so as to guide the fluid media through the braided electrode means substantially to move blood away from the braided electrode means to lessen formation of coagulum.

6. The ablation catheter of claim 3 wherein the fluid media comprises a conductive fluid media.

7. The ablation catheter of claim 6 whereby the conductive fluid media is configured to flow through the at least one braided electrode means and conduct ablative energy to the target tissue.

8. The ablation catheter of claim 7 whereby the tissue is ablated by at least ohmic energy.

9. The ablation catheter of claim 7 whereby the tissue is ablated by at least convection.

10. The ablation catheter of claim 7 whereby the tissue is ablated by at least conduction.

11. The ablation catheter of claim 1 wherein the fixed braided electrode means is exposed through at least one braided electrode aperture formed in the outer tubular structure and having a length in the range of about 1 centimeter to about 10 centimeter.

12. The ablation catheter of claim 1 wherein the braided electrode means has a length in the range of about 1 centimeter to about 10 centimeters.

13. The ablation catheter of claim 1 wherein the fixed braided electrode means extends about 60 degrees to about 180 degrees around the circumference of the catheter shaft means.

14. The ablation catheter of claim 1 wherein the braided electrode means generally defines an electrode surface that is recessed below the level of an outer surface of the outer tubular structure.

15. The ablation catheter of claim 1 wherein the braided electrode means generally defines an electrode surface that is generally flush with an outer surface of the outer tubular structure.

16. The ablation catheter of claim 1 wherein the braided electrode means is configured to at least partially contact the tissue during use.

17. The ablation catheter of claim 1 wherein the catheter shaft means defines a second lumen means.

18. The ablation catheter of claim 17 further comprising a control wire connected with the catheter shaft means and located within the second lumen means.

19. The ablation catheter of claim 18 wherein the control wire is precurved to manipulate the catheter shaft means such that the catheter shaft means forms a substantially circular shape.

20. The ablation catheter of claim 19 wherein the substantially circular shape is adapted to conform to the inner shape of the pulmonary vein.

21. The ablation catheter of claim 17 wherein the braided electrode means is connected with at least one corresponding wire adapted to connect with an ablation energy source.

22. The ablation catheter of claim 21 wherein the at least one wire is routed through the second lumen means.

23. The ablation catheter of claim 1 wherein the braided electrode means comprises at least a first braided electrode and a second braided electrode, wherein the first braided electrode and the second braided electrode are each separately connected to at least one ablation energy source.

* * * * *